US012054711B2

(12) United States Patent
Han et al.

(10) Patent No.: US 12,054,711 B2
(45) Date of Patent: Aug. 6, 2024

(54) META-STABLE OLIGONUCLEOTIDES JUNCTIONS FOR DELIVERY OF THERAPEUTICS

(71) Applicants: CITY OF HOPE, Duarte, CA (US); CALIFORNIA INSTITUTE OF TECHNOLOGY, Pasadena, CA (US)

(72) Inventors: Si-ping Han, Duarte, CA (US); Marwa Ben Haj Salah, Duarte, CA (US); Lisa Scherer, Duarte, CA (US); William A. Goddard, Pasadena, CA (US); John J. Rossi, Duarte, CA (US)

(73) Assignees: City of Hope, Duarte, CA (US); California Institute of Technology, Pasadena, CA (US)

( * ) Notice: Subject to any disclaimer, the term of this patent is extended or adjusted under 35 U.S.C. 154(b) by 1242 days.

(21) Appl. No.: 16/631,134

(22) PCT Filed: Jul. 14, 2018

(86) PCT No.: PCT/US2018/042195
§ 371 (c)(1),
(2) Date: Jan. 14, 2020

(87) PCT Pub. No.: WO2019/014656
PCT Pub. Date: Jan. 17, 2019

(65) Prior Publication Data
US 2020/0157533 A1     May 21, 2020

Related U.S. Application Data

(60) Provisional application No. 62/532,926, filed on Jul. 14, 2017.

(51) Int. Cl.
*C12N 15/11* (2006.01)
*C12N 15/113* (2010.01)
*C12Q 1/68* (2018.01)

(52) U.S. Cl.
CPC .......... *C12N 15/11* (2013.01); *C12N 2310/52* (2013.01); *C12N 2320/30* (2013.01)

(58) Field of Classification Search
None
See application file for complete search history.

(56) References Cited

U.S. PATENT DOCUMENTS

| | | |
|---|---|---|
| 6,255,469 B1 | 7/2001 | Seeman et al. |
| 6,506,559 B1 | 1/2003 | Fire et al. |
| 6,566,058 B1 | 5/2003 | Cardy |
| 6,696,285 B1 | 2/2004 | Mills et al. |
| 7,745,594 B2 | 6/2010 | Seelig et al. |
| 8,241,854 B2 | 8/2012 | Yin et al. |
| 8,318,921 B2 | 11/2012 | Pierce et al. |
| 8,404,831 B2 | 3/2013 | Natt et al. |
| 8,710,199 B2 | 4/2014 | Han et al. |
| 8,962,582 B2 | 2/2015 | Dirks |
| 9,029,524 B2 | 5/2015 | Han et al. |
| 9,115,355 B2 | 8/2015 | Han et al. |
| 9,206,419 B2 | 12/2015 | Han et al. |
| 9,297,010 B2 | 3/2016 | Eimen et al. |
| 9,518,263 B2 | 12/2016 | Han et al. |
| 9,725,715 B2 | 8/2017 | Han et al. |
| 11,643,659 B2 | 5/2023 | Marcucci et al. |
| 2005/0079504 A1 | 4/2005 | Amitai et al. |
| 2009/0234109 A1 | 9/2009 | Han et al. |
| 2010/0063134 A1 | 3/2010 | Kaemmerer |
| 2010/0112556 A1 | 5/2010 | Sampson et al. |
| 2011/0195848 A1 | 8/2011 | Roopra et al. |
| 2011/0288826 A1 | 11/2011 | Breaker et al. |
| 2012/0088815 A1 | 4/2012 | Liang |
| 2012/0101147 A1 | 4/2012 | Tsai et al. |
| 2013/0244327 A1 | 9/2013 | Puri et al. |
| 2013/0330725 A1 | 12/2013 | Saito et al. |
| 2015/0004615 A1 | 1/2015 | Pierce et al. |
| 2015/0065555 A1 | 3/2015 | Brown et al. |
| 2015/0284717 A1 | 10/2015 | Templin et al. |
| 2015/0315581 A1 | 11/2015 | Han et al. |
| 2016/0046934 A1 | 2/2016 | Han et al. |
| 2016/0130581 A1 | 5/2016 | Han et al. |
| 2016/0153036 A1 | 6/2016 | Chen et al. |

(Continued)

FOREIGN PATENT DOCUMENTS

| | | |
|---|---|---|
| EP | 2101275 A1 | 9/2009 |
| EP | 2213292 B2 | 6/2016 |

(Continued)

OTHER PUBLICATIONS

U.S. Appl. No. 63/172,030 filed Apr. 7, 2021, Han et al.
U.S. Appl. No. 63/218,862 filed Jul. 6, 2021, Si-ping Han.
U.S. Appl. No. 63/218,833 filed Jul. 6, 2021, Han et al.
U.S. Appl. No. 63/218,850 filed Jul. 6, 2021, Han et al.
U.S. Appl. No. 63/218,865 filed Jul. 6, 2021, Si-ping Han.
Adams et al., "Patisiran, an RNAi Therapeutic, for Hereditary Transthyretin Amyloidosis," The New England Journal of Medicine 2018, 379(1), 11-21.
Aduri et al., "AMBER Force Field Parameters for the Naturally Occurring Modified Nucleosides in RNA," Journal of Chemical Theory and Computation 2007, 3, 1464-1475.
American Cancer Society, "Key Statistics for Acute Myeloid Leukemia (AML)," cancer.org 2023, in 10 pages.

(Continued)

*Primary Examiner* — Sean McGarry
(74) *Attorney, Agent, or Firm* — Sheppard, Mullin, Richter & Hampton LLP

(57) ABSTRACT

Disclosed herein are multi-way oligonucleotide junctions for delivering one or more cargo molecules to a biological target and method of making such junctions. The oligonucleotide junctions are formed by two or more oligonucleotides and are stable outside the cell and easily dissociate inside the cell to release the cargo molecule(s). One or more cargo molecules as well as delivery ligand can be loaded to the junctions for targeted delivery. Also disclosed are nanostructures including one or more junctions attached to each other for delivering two or more cargo molecules.

19 Claims, 22 Drawing Sheets
Specification includes a Sequence Listing.

(56) References Cited

U.S. PATENT DOCUMENTS

| | | |
|---|---|---|
| 2017/0183652 A1 | 6/2017 | Thum et al. |
| 2018/0092997 A1* | 4/2018 | Guo .................... C12N 15/113 |
| 2018/0223344 A1 | 8/2018 | Chandrasekaran et al. |
| 2019/0153437 A1 | 5/2019 | Emerick et al. |
| 2019/0233806 A1 | 8/2019 | Garreau De Loubresse |
| 2020/0291396 A1 | 9/2020 | Zamore et al. |
| 2021/0019973 A1 | 1/2021 | Yin et al. |
| 2021/0032707 A1 | 2/2021 | Talasaz |
| 2021/0095286 A1 | 4/2021 | Weiss et al. |
| 2021/0123060 A1 | 4/2021 | Marcucci et al. |
| 2021/0230593 A1 | 7/2021 | Han et al. |
| 2023/0107117 A1 | 4/2023 | Das et al. |

FOREIGN PATENT DOCUMENTS

| | | |
|---|---|---|
| EP | 2193140 B1 | 11/2016 |
| JP | 2018-007663 A | 1/2018 |
| WO | WO2008076324 | 6/2008 |
| WO | WO2011/163526 | 12/2011 |
| WO | WO2013/075132 | 5/2013 |
| WO | WO2013/142735 | 9/2013 |
| WO | WO2019014656 | 1/2019 |
| WO | WO2019/033079 | 2/2019 |
| WO | WO2019/033083 | 2/2019 |
| WO | WO2020/033938 | 2/2020 |
| WO | WO2023/283546 | 1/2023 |
| WO | WO2023/283548 | 1/2023 |
| WO | WO2023/283550 | 1/2023 |
| WO | WO2023/283551 | 1/2023 |
| WO | WO2023/283552 | 1/2023 |
| WO | WO2023/283553 | 1/2023 |
| WO | WO2023/070057 | 4/2023 |

OTHER PUBLICATIONS

Benenson et al., "An Autonomous Molecular Computer for Logical Control of Gene Expression," Nature 2004, 429, 423-429.

Benenson, "Biomolecular Computing Systems: Principles, Progress and Potential," Nature Reviews Genetics 2012, 13, 455-468.

Beta Lab, "RNAsoft—Software for RNA/DNA secondary structure prediction and design," University of British Columbia 2023, in 1 page. http://www.rnasoft.ca/.

Bindewald et al., "Multistrand Structure Prediction of Nucleic Acid Assemblies and Design of RNA Switches," Nano Letters 2016, 16(3), 1726-1735.

Bobbin & Rossi, "RNA Interference (RNAi)-Based Therapeutics: Delivering on the Promise?" Annual Review of Pharmacology and Toxicology 2016, 56, 103-122.

Boudreau et al., "Rational Design of Therapeutic siRNAs: Minimizing Off-targeting Potential to Improve the Safety of RNAi Therapy for Huntington's Disease," Molecular Therapy 2011, 19(12), 2169-2177.

Bramsen et al., "A Large-Scale Chemical Modification Screen Identifies Design Rules to Generate siRNAs with High Activity, High Stability and Low Toxicity," Nucleic Acids Research 2009, 37(9), 2867-2881.

Bujold et al., "Optimized DNA "Nanosuitcases" for Encapsulation and Conditional Release of siRNA," Journal of the American Chemical Society 2016, 138, 14030-14038.

Camacho et al., "BLAST+: Architecture and Applications," BMC Bioinformatics 2009, 10, in 9 pages.

Cao et al., "Histone deacetylase (HDAC) inhibitors attenuate cardiac hypertrophy by suppressing autophagy," Proceedings of the National Academy of Sciences 2011, 108, 4123-4128.

Chatterjee et al., "Nucleic Acid Strand Displacement with Synthetic mRNA Inputs in Living Mammalian Cells," ACS Synthetic Biology 2018, 7(12), 2737-2741.

Chen et al., "DNA Nanotechnology from the Test Tube to the Cell," Nature Nanotechnology 2015, 10, 748-760.

Colasanti et al., "Analyzing and Building Nucleic Acid Structures with 3DNA," Journal of Visualized Experiments 2013, 74, in 10 pages.

Collingwood et al., "Chemical Modification Patterns Compatible with High Potency Dicer-Substrate Small Interfering RNAs," Oligonucleotides 2008, 18, 187-200.

Condon et al., "Optimization of an AMBER Force Field for the Artificial Nucleic Acid, LNA, and Benchmarking with NMR of L(CAAU)," The Journal of Physical Chemistry B 2014, 118, 1216-1228.

Dresselhaus & Meffert, "Cellular specificity of NF-κB function in the nervous system," Frontiers in Immunology 2019, 10, in 14 pages.

Duan et al., "A Point-Charge Force Field for Molecular Mechanics Simulations of Proteins Based on Condensed-Phase Quantum Mechanical Calculations," Journal of Computational Chemistry 2003, 24, 1999-2012.

Duda et al., "Targeting GSK3 signaling as a potential therapy of neurodegenerative diseases and aging," Expert Opinion on Therapeutic Targets 2018, 22(10), 833-848.

Efthymiou et al., "Evaluation of siRNAs that Contain Internal Variable-Length Spacer Linkages," Bioorganic & Medicinal Chemistry Letters 2012, 22, 5590-5594.

Engelen et al., "DNA-Based Control of Protein Activity," Chemical Communications 2016, 52(18), 3598-3610.

Estey, "Acute Myeloid Leukemia: 2012 Update on Diagnosis, Risk Stratification, and Management," American Journal of Hematology 2012, 87(1), 89-99.

Exiqon, "LNA™ Oligo Tools and Design Guidelines," exiqon.com 2020, in 1 page. www.exiqon.com/oligo-tools.

Extended European Search Report and Opinion dated Apr. 14, 2022 in European Patent Application No. 19846651.8.

Filipi et al., "Glial cells—The strategic targets in amyotrophic lateral sclerosis treatment," Journal of Clinical Medicine 2020, 9(1), in 47 pages.

Final Office Action dated Jul. 21, 2023 in U.S. Appl. No. 17/172,461.

First Office Action dated Feb. 27, 2023 in Chinese Patent Application No. 201880066486.5.

Glaser et al., "Anti-apoptotic Mcl-1 is Essential for the Development and Sustained Growth of Acute Myeloid Leukemia," Genes & Development 2012, 26, 120-125.

Glen Research, "Locked Analog Phosphoramidites and Supports," Glenresearch.com 2023, in 4 pages. https://www.glenresearch.com/products/labels-and-modifiers/backbone-modification/locked-analog-phosphoramidites.html.

Glen Research, "Nucleoside Analog Phosphoramidites," Glenresearch.com 2023, in 3 pages. https://www.glenresearch.com/browse/nucleoside-analog-phosphoramidites.

Glen Research, "Modification and Labeling," glenresearch.com 2023, in 6 pages. www.glenresearch.com/browse/labels-and-modifiers.

Graham et al., "Isolation, Culture, and Functional Characterization of Adult Mouse Cardiomyoctyes," JoVE 2013, 79, in 13 pages.

Green et al., "Complex Cellular Logic Computation Using Ribocomputing Devices," Nature 2017, 548(7665), 117-121.

Green et al., "To kill a microglia: a case for CSF1R inhibitors," Trends in Immunology 2020, 41(9), 771-784.

Groves et al., "Computing in Mammalian Cells with Nucleic Acid Strand Exchange," Nature Nanotechnology 2016, 11(3), 287-294.

GSRS, "Casimersen," nih.gov 2023, in 1 page. https://gsrs.ncats.nih.gov/ginas/app/beta/substances/905e0f05-b9c5-412c-a0e1-5bb898111944.

GSRS, "Eteplirsen," nih.gov 2023, in 1 page. https://gsrs.ncats.nih.gov/ginas/app/beta/substances/4d0cddf7-f088-45af-af78-27659898e442.

GSRS, "Golodirsen," nih.gov 2023, in 1 page. https://gsrs.ncats.nih.gov/ginas/app/beta/substances/e54505d8-4af5-43f6-95b4-f70effe0b457.

Guo, "The Emerging Field of RNA Nanotechnology," Nature Nanotechnology 2010, 5(12), 833-842.

Guttenplan et al., "Knockout of reactive astrocyte activating factors slows disease progression in an ALS mouse model," Nature Communications 2020, 11(1), in 9 pages.

(56) References Cited

OTHER PUBLICATIONS

Ha & Kim, "Regulation of MicroRNA Biogenesis," Nature Reviews Molecular Cell Biology 2014, 15, 509-524.
Hammond et al., "Delivery of oligonucleotide-based therapeutics: challenges and opportunities," EMBO Molecular Medicine 2021, 13(4), e13243.
Han et al., "Programmable siRNA Pro-Drugs that Activate RNAi Activity in Response to Specific Cellular RNA Biomarkers," Molecular Therapy—Nucleic Acids 2022, 27, 797-809.
Hartmann et al., "Effects of phenylephrine on calcium current and contractility of feline ventricular myocytes," American Journal of Physiology-Heart and Circulatory Physiology 1988, 255, H1173-H1180.
Heissig et al., "DNA as Tunable Adaptor for siRNA Polyplex Stabilization and Functionalization," Molecular Therapy—Nucleic Acids 2016, 5, in 10 pages.
Hill et al., "Sonic hedgehog signaling in astrocytes," Cellular and Molecular Life Sciences 2021, 78, 1393-1403.
Hochrein et al., "Conditional Dicer Substrate Formation via Shape and Sequence Transduction with Small Conditional RNAs," Journal of the American Chemical Society 2013, 135, 17322-17330.
Hochrein et al., "Signal Transduction in Human Cell Lysate via Dynamic RNA Nanotechnology," ACS Synthetic Biology 2018, 7, 2796-2802.
Hope & Trono, "Structure, Expression, and Regulation of the HIV Genome," HIV in Site 2020, in 11 pages. http://hivinsite.ucsf.edu/InSite?page=kb-OO&doc=kb-02-01-02.
Horizon, "Dharmacon reagents," horizondiscovery.com 2023, in 8 pages. http://dharmacon.horizondiscovery.com/design-center/.
Hu et al., "Therapeutic siRNA: state of the art," Signal Transduction and Targeted Therapy 2020, 5(1), in 25 pages.
Huang et al., "Activation of Wnt/β-catenin signalling via GSK3 inhibitors direct differentiation of human adipose stem cells into functional hepatocytes," Scientific Reports 2017, 7(1), in 12 pages.
Integrated DNA Technologies, "Oligo Modifications," idtdna.com 2023, in 2 pages. https://www.idtdna.com/pages/products/custom-dna-rna/oligo-modifications.
International Search Report and Written Opinion dated Jan. 4, 2019 in PCT Patent Application No. PCT/US2018/046383.
International Search Report and Written Opinion dated Jan. 25, 2023 in PCT Patent Application No. PCT/US2022/078466.
International Search Report and Written Opinion dated Nov. 25, 2019 in PCT Patent Application No. PCT/US2019/046075.
International Search Report and Written Opinion dated Nov. 26, 2018 in PCT Patent Application No. PCT/US2018/046379.
International Search Report and Written Opinion dated Oct. 4, 2022 in PCT Patent Application No. PCT/US2022/073426.
International Search Report and Written Opinion dated Oct. 27, 2022 in PCT Patent Application No. PCT/US2022/073432.
International Search Report and Written Opinion dated Sep. 14, 2022 in PCT Patent Application No. PCT/US2022/073430.
International Search Report and Written Opinion dated Sep. 23, 2022 in PCT Patent Application No. PCT/US2022/073428.
International Search Report and Written Opinion dated Sep. 28, 2022 in PCT Patent Application No. PCT/US2022/073431.
International Search Report and Written Opinion dated Sep. 28, 2022 in PCT Patent Application No. PCT/US2022/073433.
International Search Report and Written Opinion mailed Jan. 4, 2019 in PCT Patent Application No. PCT/US2018/046383.
Iwamoto et al., "Control of Phosphorothioate Stereochemistry Substantially Increases the Efficacy of Antisense Oligonucleotides," Nature Biotechnology 2017, 35(9), 845-851.
Jafar-Nejad et al., "The atlas of RNase H antisense oligonucleotide distribution and activity in the CNS of rodents and non-human primates following central administration," Nucleic Acids Research 2021, 49(2), 657-673.
Japanese Office Action dated Jul. 4, 2023 in Japanese Patent Application No. 2021531622.
Japanese Search Report dated Jun. 23, 2023 in Japanese Patent Application No. 2021531622.
Jaramillo-Botero et al., "First-principles-based multiscale, multiparadigm molecular mechanics and dynamics methods for describing complex chemical processes," Multiscale Molecular Methods in Applied Chemistry 2012, 1-42.
Jessup & Brozena, "Heart Failure," New England Journal of Medicine 2003, 348, 2007-2018.
Joe et al., "Astrocytes, microglia, and Parkinson's disease," Experimental Neurobiology 2018, 27(2), 77-87.
Kadkol et al., "Comprehensive Analysis of CBFbeta-MYH11 Fusion Transcripts in Acute Myeloid Leukemia by RT-PCR Analysis," The Journal of Molecular Diagnostics 2004, 6(1), 22-27.
Katanosaka et al., "Calcineurin Inhibits Na+/Ca2+ Exchange in Phenylephrine-treated Hypertrophic Cardiomyocytes," Journal of Biological Chemistry 2005, 280, 5764-5772.
Kim et al., "Synthetic dsRNA Dicer Substrates Enhance RNAi Potency and Efficacy," Nature Biotechnology 2005, 23(2), 222-226.
Knerr et al. "Glucagon like peptide 1 receptor agonists for targeted delivery of antisense oligonucleotides to pancreatic beta cell," Journal of the American Chemical Society 2021, 143(9), 3416-3429.
Konstam et al., "Left ventricular remodeling in heart failure: current concepts in clinical significance and assessment," JACC Cardiovasc Imaging 2011, 4(1), 98-108.
Kumar et al., "Combinatorially Inducible RNA Interference Triggered by Chemically Modified Oligonucleotides," Journal of the American Chemical Society 2011, 133, 2783-2788.
Kundu & Liu, "Function of the inv(16) Fusion Gene CBFB-MYH11," Hematology 2001, 8, 201-205.
Landry et al., "Progress in RNAi-Mediated Molecular Therapy of Acute and Chronic Myeloid Leukemia," Molecular Therapy—Nucleic Acids 2015, 4, in 23 pages.
Lee et al., "Differential Roles of Human Dicer-Binding Proteins TRBP and PACT in Small RNA Processing," Nucleic Acids Research 2013, 41(13), 6568-6576.
Lennox et al., "Improved Performance of Anti-miRNA Oligonucleotides Using a Novel Non-Nucleotide Modifier," Molecular Therapy—Nucleic Acids 2013, 2, in 19 pages.
Li et al., "Antiparallel DNA Double Crossover Molecules as Components for Nanoconstruction," Journal of the American Chemical Society 1996, 118, 6131-6140.
Lind et al., "Parameterization and Simulation of the Physical Properties of Phosphorothioate Nucleic Acids," Journal of the American Chemical Society 1998, 3, 41-54.
Liu et al., "miR-222 Is Necessary for Exercise-Induced Cardiac Growth and Protects against Pathological Cardiac Remodeling," Cell Metabolism 2015, 21, 584-595.
Loakes, "Survey and summary: The applications of universal DNA base analogues," Nucleic Acids Research 2001, 29(12), 2437-2447.
Look, "Oncogenic Transcription Factors in the Human Acute Leukemias," Science 1997, 278, 1059-1064.
Lutgen et al., "β-Catenin signaling positively regulates glutamate uptake and metabolism in astrocytes," Journal of Neuroinflammation 2016, 13, 1-13.
Macke & Case, "Modeling Unusual Nucleic Acid Structures," ACS Symposium Series, American Chemical Society 1998, 24, 379-393.
Macrae et al., "Structural Basis for Double-Stranded RNA Processing by Dicer," Science 2006, 311, 195-198.
Mark & Nilsson, "Structure and Dynamics of the TIP3P, SPC, and SPC/E Water Models at 298 K.," The Journal of Physical Chemistry A 2001, 105, 9954-9960.
Marks et al., "Histone deacetylases and cancer: causes and therapies," Nature Reviews Cancer 2001, 1(3), 194.
Mathews et al., "Expanded Sequence Dependence of Thermodynamic Parameters Improves Prediction of RNA Secondary Structure," Journal of Molecular Biology 1999, 288, 911-940.
Mathews Lab, "RNAstructure, Version 6.4," rochester.edu 2023, in 1 page. http://rna.urmc.rochester.edu/RNAstructure.html.
Mathy et al., "5'-to-3' Exoribonuclease Activity in Bacteria: Role of Rnase J1 in rRNA Maturation and 5' Stability of mRNA," Cell 2007, 129, 681-692.

(56) References Cited

OTHER PUBLICATIONS

Matsukura et al., "Phosphorothioate Analogs of Oligodeoxynucleotides: Inhibitors of Replication and Cytopathic Effects of Human Immunodeficiency Virus," Proceedings of the National Academy of Sciences 1987, 84, 7706-7710.
Meggers et al., "Synthesis and Properties of the Simplified Nucleic Acid Glycol Nucleic Acid," Accounts of Chemical Research 2010, 43(8), 1092-1102.
Millipore Sigma, "Locked Nucleic Acid," sigmaaldrich.com 2023, in 5 pages. www.sigmaaldrich.com/technical-documents/articles/biology/locked-nucleic-acids-faq.html.
Mirbase, "Stem-loop sequence hsa-mir-23a," mirbase.org 2023, in 3 pages. https://www.mirbase.org/cgi-bin/mirna_entry.pl?acc=MI0000079.
Molkentin et al., "Calcineurin-Dependent Transcriptional Pathway for Cardiac Hypertrophy," Cell 1998, 93, 215-228.
Morel et al., "Neuronal exosomal miRNA-dependent translational regulation of astroglial glutamate transporter GLT1," Journal of Biological Chemistry 2013, 288(10), 7105-7116.
Mukherjee et al., "Design of a DNA-Programmed Plasminogen Activator," Journal of the American Chemical Society 2018, 140(45), 15516-15524.
Naito & Kumiko, "Designing functional siRNA with reduced off-target effects," siRNA Design: Methods and Protocols 2013, 57-68.
Nearest Neighbor Database, "Introduction and Definitions," rochester.edu 2023, in 4 pages. https://rna.urmc.rochester.edu/NNDB/help.html.
Nearest Neighbor Database, "Version 1.02, Released Apr. 4, 11," rochester.edu 2023, in 3 pages. https://rna.urmc.rochester.edu/NNDB/index.html.
Nolan et al., "Quantification of mRNA using real-time RT-PCR," Nature Protocols 2006, 1(3), 1559-1582.
Non-Final Office Action dated Dec. 24, 2021 in U.S. Appl. No. 16/786,793.
Non-Final Office Action dated Jan. 24, 2023 in U.S. Appl. No. 17/172,461.
Non-Final Office Action dated Jun. 23, 2022 in U.S. Appl. No. 16/786,793.
Notice of Allowance dated Jan. 12, 2023 in U.S. Appl. No. 16/786,793.
Opferman et al., "Obligate Role of Anti-Apoptotic MCL-1 in the Survival of Hematopoietic Stem Cells," Science 2005, 307(5712), 1101-1104.
Orban & Izaurralde, "Decay of mRNAs Targeted by RISC Requires XRN1, the Ski Complex, and the Exosome," RNA 2005, 11, 459-469.
Owczarzy et al., "IDT SciTools: a suite for analysis and design of nucleic acid oligomers," Nucleic Acids Research 2008, 36(suppl_2), W163-W169.
Pajarillo et al., "Astrocyte-specific deletion of the transcription factor Yin Yang 1 in murine substantia nigra mitigates manganese-induced dopaminergic neurotoxicity," Journal of Biological Chemistry 2020, 295(46), 15662-15676.
Paradis et al., "Newborn Hypoxia/Anoxia Inhibits Cardiomyocyte Proliferation and Decreases Cardiomyocyte Endowment in the Developing Heart: Role of Endothelin-1," PLOS ONE 2015, 10, in 21 pages.
Pettersen et al., "UCSF Chimera-A Visualization System for Exploratory Research and Analysis," Journal of Computational Chemistry 2004, 25, 1605-1612.
Picco & Garnett, "A Road Map for Precision Cancer Medicine Using Personalized Models," Cancer Discovery 2017, 7(5), 456-458.
Plimpton, "Fast Parallel Algorithms for Short-Range Molecular Dynamics," Journal of Computational Physics 1995, 117, 1-19.
Qi et al., "HDAC8 Inhibition Specifically Targets Inv(16) Acute Myeloid Leukemic Stem Cells by Restoring p53 Acetylation," Cell Stem Cell 2015, 17(5), 597-610.
Qiagen, "Tm Prediction," qiagen.com 2020, in 1 page. https://www.qiagen.com/US/service-and-support/learning-hub/technologies-and-research-topics/lna/custom-lna-design-and-applications/lna-design-tools-calculators/lna-oligo-tm-prediction/.
Qiagen, "LNA Oligo Optimizer," qiagen.com 2020, in 1 page. https://www.qiagen.com/us/service-and-support/learning-hub/technologies-and-research-topics/lna/custom-lna-design-and-applications/lna-design-tools-calculators/lna-oligo-optimizer/.
Red Server, "RESP ESP charge Derive server," q4md-forcefieldtools.org 2023, in 2 pages. q4md-forcefieldtools.org/REDServer/.
Restriction Requirement dated Apr. 30, 2021 in U.S. Appl. No. 16/786,793.
Restriction Requirement dated Aug. 19, 2022 in U.S. Appl. No. 17/172,461.
Restriction Requirement dated May 23, 2023 in U.S. Appl. No. 16/638,107.
Rij, "Virus meets RNAi. Symposium on Antiviral Applications of RNA Interference," EMBO Reports 2008, 9(8), 725-729.
Robinson et al., "Integrative clinical genomics of metastatic cancer," Nature 2017, 548(7667), 297-303.
Rojo et al., "GSK-3β down-regulates the transcription factor Nrf2 after oxidant damage: relevance to exposure of neuronal cells to oxidative stress," Journal of Neurochemistry 2008, 105(1), 192-202.
Sano et al., "Effect of asymmetric terminal structures of short RNA duplexes on the RNA interference activity and strand selection," Nucleic Acids Research 2008, 36, 5812-5821.
Scherer et al., "Optimization and Characterization of tRNA-shRNA Expression Constructs," Nucleic Acids Research 2007, 35(8), 2620-2628.
Schlegel et al., "Chirality Dependent Potency Enhancement and Structural Impact of Glycol Nucleic Acid Modification on siRNA," Journal of the American Chemical Society 2017, 139, 8537-8546.
Second Office Action dated Sep. 20, 2023 in Chinese Patent Application No. 201880066486.5.
Seeman, "DNA in a Material World," Nature 2003, 421, 427-431.
Setten et al., "The Current State and Future Directions of RNAi-Based Therapeutics," Nature Reviews Drug Discovery 2019, 18, 421-446.
Silverman, "Control of Macromolecular Structure and Function Using Covalently Attached Double-Stranded DNA Constraints," Molecular BioSystems 2007, 3, 24-29.
Srinivas et al., "On the Biophysics and Kinetics of Toehold-Mediated DNA Strand Displacement," Nucleic Acids Research 2013, 41(22), 10641-10658.
Srinivasan et al., "Alzheimer's patient microglia exhibit enhanced aging and unique transcriptional activation," Cell Reports 2020, 31(13), in 20 pages.
Supplementary European Search Report and European Search Opinion dated Apr. 8, 2021 in European Patent Application No. 18844244.6.
Sussman et al., "Prevention of Cardiac Hypertrophy in Mice by Calcineurin Inhibition," Science 1998, 281, 1690-1693.
Tham et al., "Pathophysiology of cardiac hypertrophy and heart failure: signaling pathways and novel therapeutic targets," Archives of Toxicology 2015, 89, 1401-1438.
The Nupack Team, "Nupack Cloud Alpha," nupack.org 2023, in 1 page. http://nupack.org.
Theoretical Biochemistry Group, "The ViennaRNA Package," Universitat Wien 2023, in 7 pages. https://www.tbi.univie.ac.at/RNA/.
Tolstrup et al., "OligoDesign: Optimal Design of LNA (Locked Nucleic Acid) Oligonucleotide Capture Probes for Gene Expression Profiling," Nucleic Acids Research 2003, 31 (13), 3758-3762.
Trivedi et al., "Hdac2 regulates the cardiac hypertrophic response by modulating Gsk3J3 activity," Nature Medicine 2007, 13, 324-331.
Turner & Mathews, "NNDB: the nearest neighbor parameter database for predicting stability of nucleic acid secondary structure," Nucleic Acids Research 2010, 38(suppl_1), D280-D282.
Vargas & Johnson, "The Nrf2—ARE cytoprotective pathway in astrocytes," Expert Reviews in Molecular Medicine 2009, 11, in 20 pages.
Verma & Eckstein, "Modified oligonucleotides: synthesis and strategy for users," Annual Review of Biochemistry 1998, 67(1), 99-134.

(56) References Cited

OTHER PUBLICATIONS

Wang et al., "Development and Testing of a General Amber Force Field," Journal of Computational Chemistry 2004, 25, 1157-1174.
Wikipedia, "Locked Nucleic Acid," eikipedia.org 2023, in 4 pages. https://en.wikipedia.org/wiki/Locked_nucleic_acid.
X3DNA, "x3DNA-DSSR: The Next Generation of 3DNA with Unmatched Features for RNA Structural Bioinformatics," x3dna. org 2023, in 3 pages. https://x3dna.org/articles/seeing-is-understanding-as-well-as-believing.
Xiao et al., "miR-31a-5p promotes postnatal cardiomyocyte proliferation by targeting RhoBTB1," Experimental & Molecular Medicine 2017, 49, in 10 pages.
Yang et al., "Studies of the 5' Exonuclease and Endonuclease Activities of CPSF-73 in Histone Pre-mRNA Processing," Molecular and Cellular Biology 2009, 29(1), 31-42.
Yurke et al., "A DNA-Fuelled Molecular Machine Made of DNA," Nature 2000, 406, 605-608.
Zhang et al., "Mcl-1 is Critical for Survival in a Sub groupof Non-Small-Cell Lung Cancer Cell Lines," Oncogene 2011, 30, 1963-1968.
Zhou et al., "Selection, Characterization and Application of New RNA HIV gp 120 Aptamers for Facile Delivery of Dicer Substrate siRNAs into HIV Infected Cells," Nucleic Acids Research 2009, 37(9), 3094-3109.
Afonin, K. A., et al., "Design and self-assembly of siRNA-functionalized RNA nanoparticles for use in automated hanomedicine," Nat. Protoc. 6(12):2022-2034 (2012).
Avino, A., et al., "Oligonucleotide-peptide conjugates: Solid-phase synthesis under acidic conditions and use in ELISA assays," Molecules 17:13825-13843 (2012).
Bhatia, D., et al., "A synthetic icosahedral DNA-based host-cargo complex for functional in vivo imaging," Nat. Commun. 2:339 (2011).
Chojnowski, G., et al., "RNA bricks—a database of RNA 3D motifs and their interactions," Nucl. Acids Res. 42:D123-D131 (2014).
Dirks, R. M., et al., "A partition function algorithm for nucleic acid secondary structure including pseudoknots," J. Comput. Chem. 24:1664-1677 (2003).
Dirks, R. M., et al., "An algorithm for computing nucleic acid base-pairing probabilities including pseudoknots," J. Comput. Chem. 25:1295-1304 (2004).
Dirks, R. M., et al., "Paradigns for computational nucleic acid design," Nucl. Acids Res. 32(4):1392-1403 (2004).
Dirks, R. M., et al., "Thermodynamic analysis of interacting nucleic acid strands," SIAM Rev. 49(I):65-88 (2007).
Dowdy, S. F., "Overcoming cellular barriers for RNA therapeutics," Nat. Biotechnol. 35(3):222-229 (2017).
Fleige, E., et al., "Stimuli-responsive polymeric nanocarriers for the controlled transport of active compounds: Concepts and applications," Adv. Drug Deliv. Rev. 64:866-884 (2012).
Gawande, B. N., et al., "Selection of DNA aptamers with two modified bases," PNAS 114(11):2898-2903 (2017).
Keum, J.W., et al., "Design, assembly, and activity of antisense DNA nanostructures," Small 7(24):3529-35358 (2011).
Khvorova, A., et al., "The chemical evolution of oligonucleotide therapies of clinical utility," Nat. Biotechnol. 35(3):238-248 (2017).
Lee, H., et al., "Molecularly self-assembled nucleic acid nanoparticles for targeted in vivo siRNA delivery," Nat. Nanotechnol. 7(6):389-393 (2014).
Lu, J., et al., "Linkers having a crucial role in antibody-drug conjugates," Int. J. Mol. Sci. 17:561 (2016).
Pi, F., et al., "RNA nanoparticles harboring annexin A2 aptamer can target ovarian cancer for tumor-specific doxorubicin delivery," Nanomedicine 13(3):1183-1193 (2017).
Rothemund, P. W. K., "Folding DNA to create nanoscale shapes and patterns," Nature 440:297-302 (2006).
Sabir, T., et al., "Branchpoint expansion in a fully complementary three-way DNA junction," J. Am. Chem. Soc. 134(14):6280-6285 (2012).
Shu, D., et al., "Thermodynamically stable RNA three-way junctions as platform for constructing multi-functional nanoparticles for delivery of therapeutics," Nat. Nanotechnol. 6(10):658-667 (2012).
Shu, D., et al., "Programmable folding of fusion RNA in vivo and in vitro driven by pRNA 3WJ motif of phi29 DNA packaging motor," Nucl. Acids Res. 42(2):e10 (2014).
Shukla, S., et al., "Exploring chemical modifications for siRNA therapeutics: a structural and functional outlook," ChemMedChem 5:328-349 (2010).
United States Patent and Trademark Office, International Search Report and Written Opinion dated Sep. 20, 2018 for PCT/US18/42195, 9 pages.
Walsh, A. S., et al., "DNA cage delivery to mammalian cells," ACS Nano 5(7):5427-5432 (2011).
Wolfe, B. R., et al., "Sequence design for a test tube of interacting nucleic acid strands," ACS Synth. Biol. 4:1086-1100 (2015).
Wolfe, B. R., et al., "Constrained multistate sequence design for nucleic acid reaction pathway engineering," J. Am. Chem. Soc. 139:3134-3144 (2017).
Zadeh, J. N., et al., "NUPACK: Analysis and design of nucleic acid systems," J. Comput. Chem. 32:170-173 (2011).
Zadeh, J. N., et al., "Nucleic acid sequence design via efficient ensemble defect optimization," J. Comput. Chem. 32:439-452 (2011).
Zhang, F., et al., "Structural DNA nanotechnology: State of the art and future perspective," J. Am. Chem. Soc. 136:11198-11211 (2014).
Dai, Yifan et al. "Strand displacement strategies for biosensor applications." Trends in biotechnology 37.12 (2019): 1367-1382.
De Windt, Leon J., et al. "Targeted inhibition of calcineurin attenuates cardiac hypertrophy in vivo." Proceedings of the National Academy of Sciences 98.6 (2001): 3322-3327.
Fiedler et al., "Quantitative RT-PCR Methods for Mature microRNA Expression Analysis," RT-PCR Protocols: Second Edition 2010, 49-64.
Fornace, Mark E., et al. "NUPACK: analysis and design of nucleic acid structures, devices, and systems." (2022).
GENECARDS: The Human Gene Database. Myosin Heavy Chain 7 (MYH7), available at: "www.genecards.org/cgi-bin/carddisp.pl?gene=MYH7", last accessed on Apr. 12, 2024 printed in 34 pages.
Gethers, Matthew Leroy. Therapeutic Opportunities and Approaches to Sequence Control for Nucleic Acids. California Institute of Technology, 2018.
Holohan et al., "Cancer drug resistance: an evolving paradigm," Nat Rev Cancer 2013, 13(10), 714-26.
Huang, Yong, et al. "Biological functions of microRNAs: a review." Journal of physiology and biochemistry 67 (2011): 129-139.
National Library of Medicine. National Center for Biotechnology Information. Reference Sequence: NM_001527.3. *Homo sapiens* histone deacetylase 2 (HDAC2), transcript variant 1, mRNA. Available at: "www.ncbi.nlm.nih.gov/nuccore/NM_001527.3", last accessed on Apr. 12, 2024 printed in 7 pages.
Non-final office action dated Jan. 8, 2024 in U.S. Appl. No. 16/638,107.
Office action dated Jan. 9, 2024 in Japanese Patent Application No. 2021-531622.
Office action dated Jul. 4, 2023 in Japanese Patent Application No. 2021-531622.
Office Action dated Nov. 11, 2023 in Chinese Patent Application No. 201980067384.X.
Office Action from U.S. Appl. No. 17/172,461 dated Aug. 19, 2022.
RESP ESP charge Derive (RED) Server Development. Avaibale at: "https://upjv.q4md-forcefieldtools.org/REDServer-Development/" last accessed on Apr. 12, 2024, printed in 2 pages.
SFOLD—Software for Statistical Folding and Studies of Regulatory RNAs, available at "https://sfold.wadsworth.org/cgi-bin/index.pl" last accessed on Jan. 17, 2014, printed in 3 pages.
Simmel, Friedrich C. et al., "Principles and applications of nucleic acid strand displacement reactions." Chemical reviews 119.10 (2019): 6326-6369.
Thermo Fisher Scientific Inc. Ppp3ca (protein phosphatase 3, catalytic subunit, alpha isoform) siRNA ID s72075, available at: "https://www.thermofisher.com/order/genome-database/browse/sirna/keyword/s72075" Last accessed on Apr. 12, 2024 printed in 2 pages.

(56) References Cited

OTHER PUBLICATIONS

Thole, Theresa M., et al. "Neuroblastoma cells depend on HDAC11 for mitotic cell cycle progression and survival." Cell death & disease 8.3 (2017): e2635-e2635.
UNAFold, available at: "http://www.unafold.org/", last accessed on Jan. 17, 2024 printed in 1 page.
Wang, Dong, et al. "Atrial natriuretic peptide affects cardiac remodeling, function, heart failure, and survival in a mouse model of dilated cardiomyopathy." Hypertension 63.3 (2014): 514-519.
Zhao et al., "Conditional RNA Interference in gene therapy research progress," Journal of Huazhong University of Science and Technology 2014, 43(4), 478-481.

* cited by examiner

Figure 18
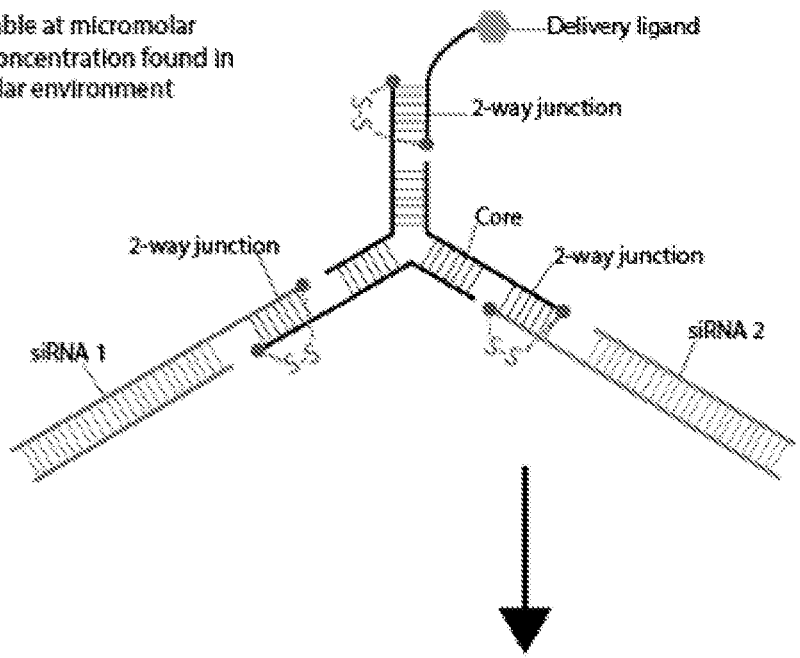
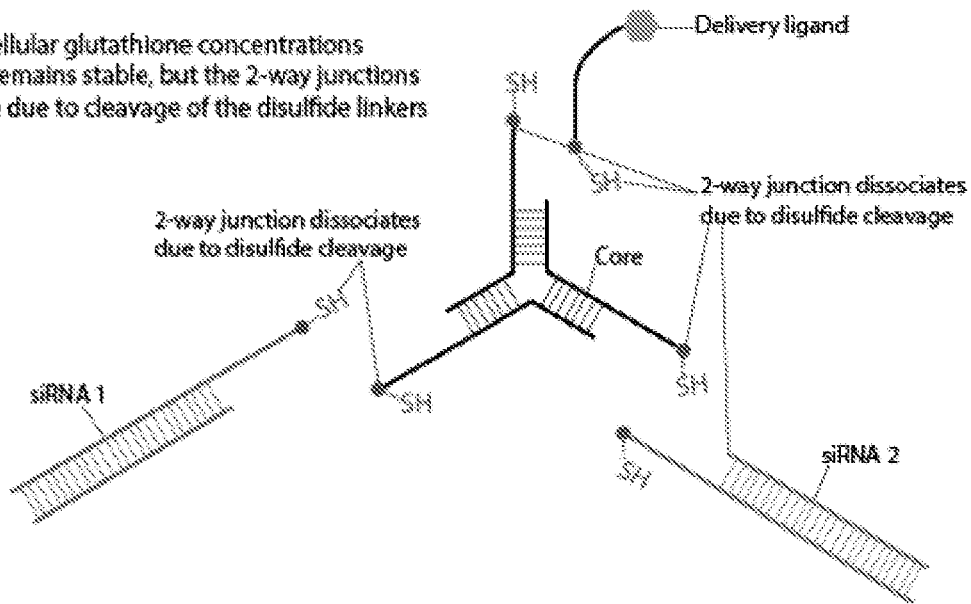

Figure 19

1. The three component strands of the 3wj core are reacted with sulfo-NHS-ester - DBCO linkers to attach DBCO to primary amines at the ends of the strands.

2. Excess linkers are removed by ethanol precipitation.

3. DBCO-labeled strands are base-paired in the thermocycler resulting in this structure

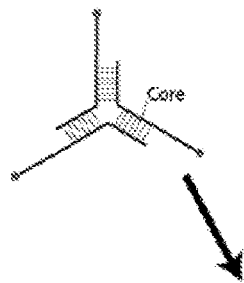

Separately, the delivery ligand and the siRNAs are each reacted with sulfo-NHS-ester-DBCO linkers (Step1), purified by ethanol precipitation to remove excess then with Azide-disulfide linker (Step 2)

Step 1: Addition of sulfo-NHS-ester-DBCO linker

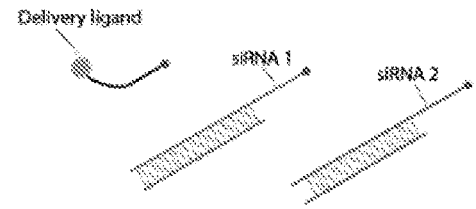

Step 2: Addition of Azide-disulfide linker

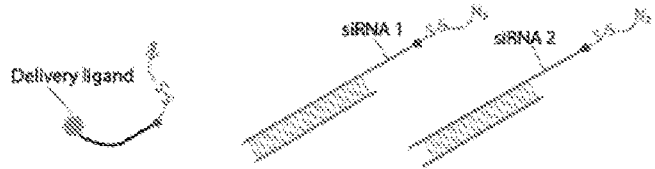

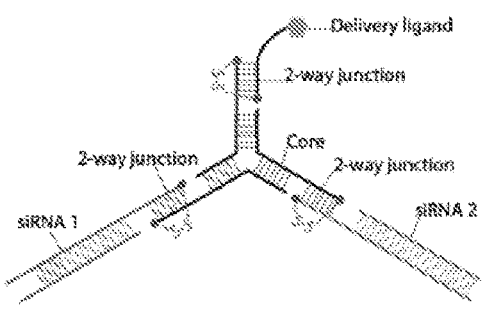

```
                         SEQUENCE LISTING

<160> NUMBER OF SEQ ID NOS: 7

<210> SEQ ID NO 1
<211> LENGTH: 126
<212> TYPE: DNA
<213> ORGANISM: Artificial Sequence
<220> FEATURE:
<223> OTHER INFORMATION: siRNA strand

<400> SEQUENCE: 1
tttctttcat ctaccaccgc atcggaagtg ccggacgcct ttcctagtcc ggcacttccg      60
agctgcggtg actgaagagc aagacagtca ccgcagccat gttacggcga catcattcac     120
ctcact                                                                126

<210> SEQ ID NO 2
<211> LENGTH: 49
<212> TYPE: DNA
<213> ORGANISM: Artificial Sequence
<220> FEATURE:
<223> OTHER INFORMATION: siRNA strand

<400> SEQUENCE: 2
gtcgccgtaa ctacaatcaa cgccacctct ccacctccaa accaccaac                  49

<210> SEQ ID NO 3
<211> LENGTH: 13
<212> TYPE: DNA
<213> ORGANISM: Artificial Sequence
<220> FEATURE:
<223> OTHER INFORMATION: siRNA strand

<400> SEQUENCE: 3
cggcgagtag cgg                                                         13

<210> SEQ ID NO 4
<211> LENGTH: 126
<212> TYPE: RNA
<213> ORGANISM: Artificial Sequence
<220> FEATURE:
<223> OTHER INFORMATION: siRNA strand

<400> SEQUENCE: 4
uuucuuucau cuaccaccgc aucggaagug ccggacgccu uuccuagucc ggcacuuccg      60
```

```
agcugcggug acugaagagc aagacaguca ccgcagccau guuacggcga caucauucac       120
cucacu                                                                   126

<210> SEQ ID NO 5
<211> LENGTH: 49
<212> TYPE: RNA
<213> ORGANISM: Artificial Sequence
<220> FEATURE:
<223> OTHER INFORMATION: siRNA strand

<400> SEQUENCE: 5
gucgccguaa cuacaaucaa cgccaccucu ccaccuccaa accaccaac                    49

<210> SEQ ID NO 6
<211> LENGTH: 43
<212> TYPE: RNA
<213> ORGANISM: Artificial Sequence
<220> FEATURE:
<223> OTHER INFORMATION: siRNA strand

<400> SEQUENCE: 6
cguugauugc ucgccgacuu uccaccaccu ccacucuaca cac                          43

<210> SEQ ID NO 7
<211> LENGTH: 13
<212> TYPE: RNA
<213> ORGANISM: Artificial Sequence
<220> FEATURE:
<223> OTHER INFORMATION: siRNA strand

<400> SEQUENCE: 7
cggcgaguag cgg                                                           13
```

META-STABLE OLIGONUCLEOTIDES JUNCTIONS FOR DELIVERY OF THERAPEUTICS

PRIORITY CLAIM

This application is a U.S. national phase application of International Application No. PCT/US2018/042195, filed Jul. 14, 2018, which claims priority to U.S. Provisional Application No. 62/532,926, filed Jul. 14, 2017, both of which are incorporated by reference herein in their entirety, including drawings.

STATEMENT REGARDING FEDERALLY SPONSORED RESEARCH OR DEVELOPMENT

This invention was made with government support under Grant Number 1332411, awarded by National Science Foundation and Grant Number AI029329, awarded by National Institutes of Health (NIH). The government has certain rights to the invention.

BACKGROUND

Over the past three decades, researchers have advanced the construction of oligo-nanostructures from low to high levels of complexity (1-3) and nano-architectures using DNA or RNA are beginning to be used for imaging and therapeutic delivery purposes (4-6). However, the measured biological activity of the delivery systems has so far not suggested revolutionary improvements in clinical efficacy. Delivery is one of the most challenging technical barriers for effective use of oligonucleotide therapeutics (OT) in vivo. Recent studies have demonstrated that simple nucleic acid nanostructures can act as molecularly uniform, multivalent carrier platforms for therapeutic cargos and cell targeting or delivery ligands. Although this approach has significant promise, much remains unknown regarding the effects of carrier nanostructures on the (I) in vivo distribution and pharmacokinetics, (II) cell entry and endosomal escape and (III) cytoplasmic processing of therapeutic cargos such as small interfering RNAs (siRNA). Most of the existing designs demonstrated the outstanding thermodynamic stability they were designed for, but preliminary work carried out showed that the rate of dicer processing is significantly decreased when the siRNA is attached to adjacent oligonucleotide duplexes. Stable nanostructure assemblies can have a significant detrimental effect on the biological processing of the therapeutic cargo in the cytosol, and this over-looked issue might be critical to improving the biological activity. Existing nanostructures share one disadvantage in common: Since they do not dissociate inside the cell they can be stable not only in circulation but also in the cytosol, thereby preventing release of the therapeutic agent in the cytosol.

The nanostructures, methods, and technology described in this disclosure satisfy the needs in the art by providing a novel oligonucleotide structure that significantly improves delivery efficiency and biological activity of the therapeutic agents.

SUMMARY

In one aspect, this disclosure relates to an oligonucleotide junction for delivering a cargo molecule to a biological target, e.g., the cytosol of a cell, endosomes and lysosomes. The oligonucleotide junction comprises two or more oligonucleotides, wherein at least a portion of each oligonucleotide complementarily binds to a portion of another oligonucleotide to form a double-stranded arm, and wherein each oligonucleotide comprises or is attached to at least one single-stranded overhang. In some embodiments, the oligonucleotide includes a DNA, an RNA, and a synthetic oligonucleotide. In some embodiments, the oligonucleotide junction comprises two or more single stranded overhangs functioning as anchor strands, which can bind the same cargo molecule or different cargo molecules. In some embodiments, the cargo molecule includes an siRNA, a DNA or RNA aptamer, a drug or prodrug, a small molecule, an antibody, a nanoparticle, a radioisotope, and a fluorophore. In some embodiments, each double-stranded arm has a length of between 3 and 15 base pairs. In some embodiments, different arms of the same oligonucleotide junction have the same length. In other embodiments, different arms of the same oligonucleotide junction have different lengths. In some embodiments, at least one arm of the oligonucleotide is crosslinked. For example, at least one arm can be crosslinked at the extremity by a cross-linker containing a disulfide bond such as DTSSP. In some embodiments, at least one single-stranded overhang is an anchor strand that binds an anchor pairing (AP) strand comprising or attached to a cargo molecule. In some embodiments, at least one single-stranded overhang is an anchor strand that binds a delivery ligand for targeting a specific type of cells. In some embodiments, the junction can deliver one or more siRNAs, and at least one single-stranded overhang is a guide strand that binds a passenger strand. In some embodiments, the oligonucleotide junction can be further chemically modified to improve stability and/or affinity for a desired target. In some embodiments, two or more oligonucleotide junctions can be attached or linked to form a nanostructure.

In some embodiments, the oligonucleotide junction comprises two oligonucleotides to form a two-way junction, wherein at least a portion of the oligonucleotides complementarily bind to each other to form at least one arm. In some embodiments, a double-stranded arm is formed by complementary binding of a portion of each oligonucleotide in the middle such that both ends of each oligonucleotide are single-stranded overhangs in the two-way junction. Alternatively, the double-stranded arm can be at either end of the oligonucleotide such that the other end of the oligonucleotide is a single-stranded overhang in the two-way junction. In other embodiments, the double-stranded arms can be at both ends of the oligonucleotides and a single-stranded overhang can be attached to each oligonucleotide.

In some embodiments, the oligonucleotide junction is a three-way junction including an oligonucleotide core formed by three oligonucleotides, wherein the two ends of each oligonucleotide complementarily bind to the two other oligonucleotides, and wherein at least a portion of each end of each oligonucleotide complementarily binds at least a portion of one end of each of the two other oligonucleotides to form a double-stranded arm such that the three-way junction comprises three double-stranded arms.

In some embodiments, the oligonucleotide junction is an N-way junction formed by at least 3, at least 4, at least 5, at least 6, at least 7, at least 8, at least 9, at least 10 oligonucleotides, wherein each oligonucleotide complimentarily binds to two different adjacent oligonucleotides such that an N-way junction comprises N double-stranded arms, wherein N is an integer greater than 2. In some embodiments, one or more arms can be linked by terminal loops.

In some embodiments, a nanostructure can be formed by attaching two or more junctions disclosed herein to each other. In some embodiments, two, three, four, five, six, or more junctions are attached to each other to form a nanostructure. In some embodiments, disclosed herein is a nanostructure comprising a core of a three-way, four-way, five-way, or six-way junction, and a two-way junction attached to each arm of the three-way, four-way, five-way, or six-way junction core. For example, a nanostructure disclosed herein comprises a three-way junction, wherein each arm of the three-way junction is attached to a two-way junction such that the three-way junction core is attached to three two-way junctions. In some embodiments, each of the two-way junctions has one end attached to the three-way, four-way, or five-way junction core and the other end loaded with or attached to a cargo molecule such as an siRNA or a delivery ligand targeting a cell. In some embodiments, the multi-way junction core of the nanostructure is stabilized by chemical modifications such as 2'-O-methyl modification and lock nucleic acid bases (LNA).

In another aspect, this disclosure relates to a method of producing an oligonucleotide junction. The method includes annealing two or more oligonucleotides to assemble an oligonucleotide junction, and crosslinking the assembled oligonucleotide junction. The method can further include attaching one or more single-stranded anchor strands to one or more oligonucleotides. In some embodiments, one or more anchor strands are attached to one or more oligonucleotides before annealing. In some embodiments, the method further includes chemically modifying the oligonucleotide junction.

In another aspect, this disclosure relates to a method of targeted delivery of one or more cargo molecules to a subject comprising loading the cargo molecules to the multi-way oligonucleotide junction disclosed herein, and administering the loaded oligonucleotide junction to the subject.

In yet another aspect, this disclosure relates to pharmaceutical or diagnostic compositions comprising one or more oligonucleotide junctions loaded with one or more cargo molecules for therapeutic or diagnostic uses.

BRIEF DESCRIPTION OF THE DRAWINGS

FIG. 18 illustrates the dissociation process of a nanostructure disclosed herein in the intracellular environment.

FIG. 19 illustrates the multi-step synthesis process for a nanostructure including a three-way junction core, with each arm attached to a two-way junction.

DETAILED DESCRIPTION

Disclosed herein are oligonucleotide-nanostructures for delivering combinations of therapeutics such as siRNAs, DNA or RNA aptamers, drugs or prodrugs, small molecules, antibodies, nanoparticles, radioisotopes, fluorophores, etc. These nanostructures augment advantages of oligonucleotide self-assembly with the utilization of cleavable crosslinkers to combine high stability in systemic circulation with spontaneous disassembly and therapeutics release in the cytosol, which substantially improves the biological activity.

Oligonucleotides such as DNA and RNA strands are easily programmable resulting in well-defined molecular assemblies with precisely controlled size, cargo molecule density, and surface ligand presentation. There are existing DNA/RNA nanostructures for therapeutic delivery purposes. For example, an RNA nanoring structure and a trivalent RNA nanoparticle can be used for delivering cargo molecules (7-8). In these structures, the cargo molecules are attached to the junction of each structure and folic acid is used as delivery ligand. Some examples of the cargo molecules delivered by these structures include siRNAs (surviving, metallothionein-IIA, BRACAA1), ribozymes (HBV-cleaving ribozyme), and aptamers (malachite green dye aptamer). Lee et al. disclose a tetrahedral DNA nanoparticle having cargo molecules (e.g. luciferase-siRNAs) attached to the junction of the tetrahedral DNA nanoparticle and also using folic acid as delivery ligand (9). Additionally, Sabir et al. disclose a DNA 3-way junction which is in a Y-shaped, pyramidal structure and has an unpaired cavity-like central point in solution (3). Despite the progress in the art, DNA and RNA nanostructures have not reached a sufficient level of biological activity to obtain significantly improved clinical outcome.

Figure 1:
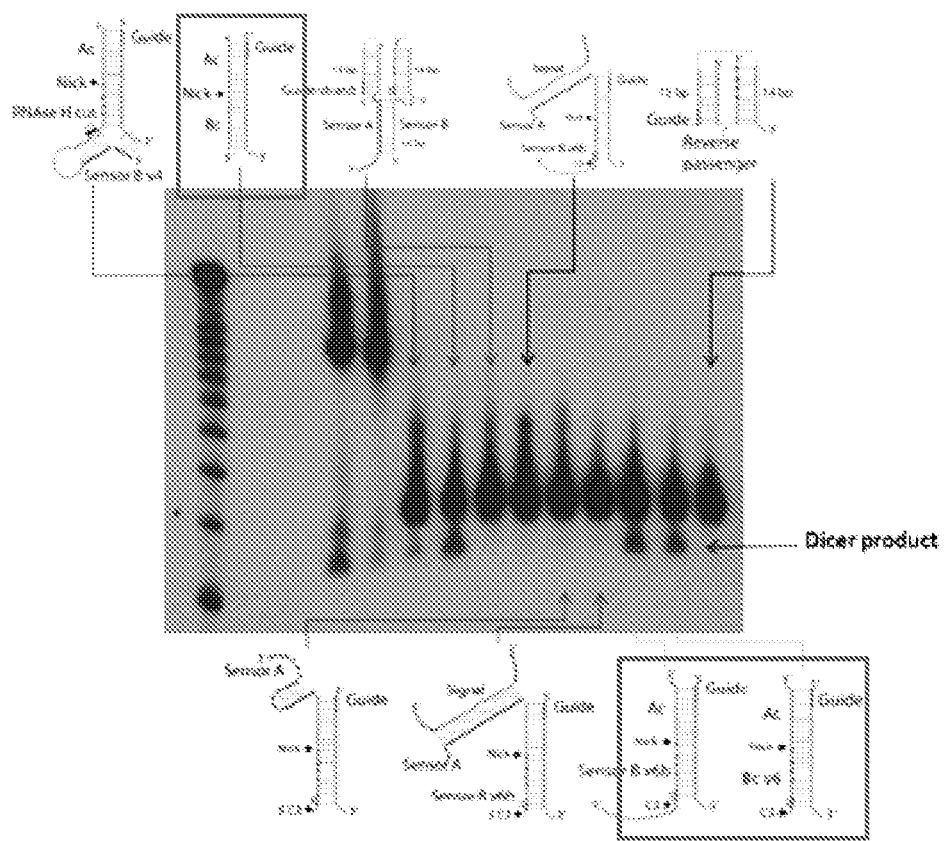
FIG. 1 shows the Northern Blot analysis of the guide strand of various putative siRNA complexes 24 hours post-transfection of Dicer substrates in HCT116. Dicer processing was reduced when siRNA was attached to adjacent oligo duplexes.

Dicer is an enzyme that cleaves double-stranded RNA and pre-microRNA into small interfering RNA (siRNA) and microRNA, thereby facilitating RNA interference. As shown in FIG. 1, the experiment carried out herein demonstrates that the dicer processing was significantly decreased when the siRNA was attached to adjacent oligonucleotide duplexes. Surprisingly, the Dicer processing of a synthetic Dicer substrate can be slowed or inhibited by the presence of additional oligonucleotide duplexes or structures connected to the synthetic Dicer substrate. This finding indicates that the conventional oligonucleotide nanostructures used to deliver siRNAs and Dicer substrates can compromise the biological activities of the siRNAs or synthetic Dicer substrates in the cells. This experiment demonstrates that the existing nanostructures have limited clinical uses because they are difficult to dissociate in the cell. Therefore, there is a need to provide a delivery structure that is stable in circulation while easy to dissociate upon delivery to a biological target, e.g., in the cytosol, to release the cargo molecules.

Thus, disclosed herein are nanostructures, e.g., a metastable oligonucleotide junction that dissociates in the cytosol upon degradation of reducible cross-linkers. As used herein, "metastable" means that the oligonucleotide junction is stable during storage or circulation until it enters a specific biological environment where the junction becomes unstable and readily dissociates. For example, when the oligonucleotide junction specifically targets the cytosol, linkers containing disulfide bonds can be used such that the junction dissociates in the presence of high intracellular concentration of reduced glutathione causing reducing of the disulfide bonds. In another example, oligonucleotide junctions containing pH cleavable linkers can be used to target endosomes or lysosomes such that the junctions dissociate at a lower pH condition. As for oligonucleotides containing enzyme cleavable linkers, dissociation can occur in the cytosol, the endosome, the lysosome, or even extracellular environment where enzymes such as matrix metalloproteases that are present in specific tissues such as tumors or regions of local inflammation can cleave specific enzymatic substrates.

Multi-Way Oligonucleotide Junctions

In one aspect, this disclosure relates to an oligonucleotide junction. The junction disclosed herein can be used for nano-based simultaneous, multifunctional delivery of various cargo molecules. The junction is formed by two or more oligonucleotides, including DNA, RNA, and synthetic oligonucleotides. Multi-way junctions can be formed by multiple oligonucleotides. For example, a two-way junction can be formed by two oligonucleotides via complimentary binding of a portion of the oligonucleotides to form a double-stranded arm. Likewise, a higher level oligonucleotide junction such as a three-way, four-way, five-way, six-way, seven-way, eight-way, nine-way, ten-way junction having multiple double-stranded arms can be formed by 3, 4, 5, 6, 7, 8, 9, or 10 oligonucleotides. Higher level oligonucleotide junctions can be formed by even more oligonucleotides.

The double-stranded arms of each oligonucleotide junction can have the same length or different lengths. In some embodiments, the double-stranded arm has a length of between 4 and 15 base pairs, for example, 4 bp, 5 bp, 6 bp, 7 bp, 8 bp, 9 bp, 10 bp, 11 bp, 12 bp, 13 bp, 14 bp, or 15 bp. For a multi-way oligonucleotide junction having multiple double-stranded arms, the double-stranded arms may have the same length or different lengths. Further, one or more arms can be cross-linked by one or more cross-linkers which are degradable upon entry into cytosol.

Once administered to a subject, the oligonucleotide junctions disclosed herein are stable in circulation but can easily dissociate upon entry into cytosol to release the cargo molecule. The stability of the oligonucleotide junctions can be optimized by varying different factors. For example, the length of the double-stranded arm can be optimized: if the double-stranded arm is too short, the junction may be unstable and dissociate before entry into cytosol; if the double-stranded arm is too long, the junction may be too stable and fail to dissociate in the cytosol to release the cargo molecule. Cross-linking one or more double-stranded arms with one or more cross-linkers can further improve the stability of the oligonucleotides. In some embodiments, the cross-linker is a reducible cross-linker which degrades upon entry into cytosol. The number of double-stranded arms that are cross-linked, the location of the cross-linker in the double-stranded arm, the type of the cross-linker, and/or the number of the cross-linkers in each double-stranded arm can be varied to achieve the desired stability of the oligonucleotide junction. For example, an oligonucleotide junction having a longer double-stranded arm may require less strength of crosslinking.

The multi-way oligonucleotide junctions disclosed herein has a size smaller than the prior-art oligonucleotide nanostructures. Due to their large sizes, the prior-art nanostructures are difficult to dissociate to release the cargo molecules. The smaller size of the oligonucleotide junctions disclosed herein is also beneficial for extravasation and tissue penetration. Moreover, smaller junctions lead to faster renal clearance. If a larger size of nanostructures is required, the junctions disclosed herein can be made bigger by complexation, by adding pendant molecules, e.g., PEG, by attaching to an antibody, or by attaching to large molecules such as cholesterols such that the junction can be associated with serum proteins such as albumins.

In some embodiments, the junctions disclosed herein can be self-assembled at a lower temperature such as at 4° C. by Watson-Crick base-pairing and then covalently stabilized by crosslinkers that bridge proximal attachment sites on complementary strands. The crosslinkers reinforce the junctions against disassembly at a higher temperature such as at 37° C. and biochemical degradation during delivery, and allow the constructs to be unusually compact compared to normal nucleic acid junctions stabilized by Watson-Crick base-pairing alone. Thus, the junctions disclosed in these embodiments have a more compact 3D structure and reduced amount of negative charge to further facilitate the in vivo delivery of these junctions. By using cleavable, reducible, or acid labile crosslinkers, the junction can be engineered to dissociate at a specific stage of the delivery process. For example, disulfide-based crosslinkers can be used for assembly and efficient crosslinking to obtain compact junctions. The junctions disclosed herein are highly stable in extracellular media but can readily dissociate in reducing environments such as the cytosol. Junctions with two or more arms can carry two or more different siRNAs. This allows RNAi knockdown against two or more independent targets in the same cell. When an siRNA is delivered with a dissociating junction along with other siRNAs, its RNAi activity is not decreased compared to the same siRNA delivered on its own.

Figure 2A:
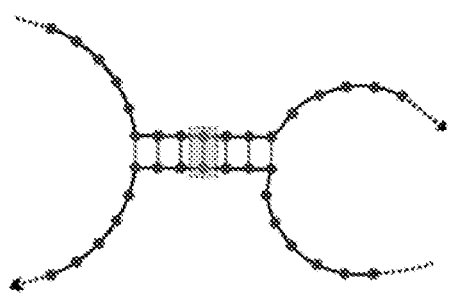
FIGS. 2A-2C illustrate examples of various two-way junctions. Single-stranded overhangs can be attached to the oligonucleotides and act as cargo molecule attachment sites. The gray box in the junction indicates a possible crosslinking position.
Figure 2B:
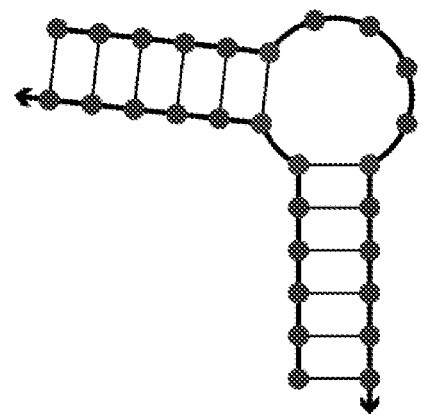
Figure 2C:
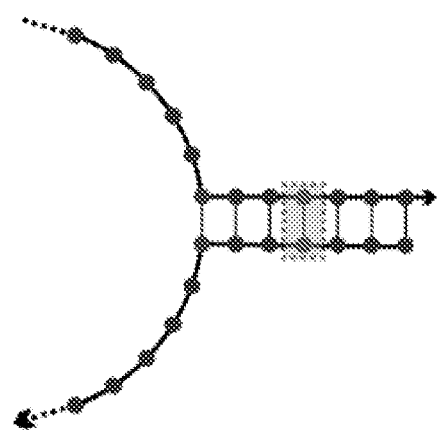

FIGS. 2A-2C illustrate various examples of two-way oligonucleotide junctions, each oligonucleotide can be attached to a single-stranded overhang functioning as cargo molecule attachment sites. For example, the middle portions of the oligonucleotides complementarily bind to each other to form a double-stranded arm such that both ends of each oligonucleotide are single-stranded overhangs (FIG. 2A). In other embodiments, the double-stranded arms can be at both ends of the oligonucleotides with non-base-paired bases in the center, and a single-stranded overhang can be attached to each oligonucleotide (FIG. 2B). Alternatively, an end portion of the oligonucleotide complementarily binds to an end portion of the other oligonucleotide to form a double-stranded arm such that the other non-binding end of each oligonucleotide is a single-stranded overhang (FIG. 2C). In view of this disclosure, one of ordinary skill in the art can select a desired configuration for a particular two-way junction or a higher level junction. In some embodiments, the single-stranded overhang comprises or attaches to a cargo molecule or to a ligand targeting a specific cell type. In some embodiments, the single-stranded overhang attaches to another oligonucleotide junction. The double-stranded arm has a length of 4 bp, 5 bp, 6 bp or 7 bp. Furthermore, nucleotides at any location of the double-stranded arm can be cross-linked to increase stability.

Figure 3:
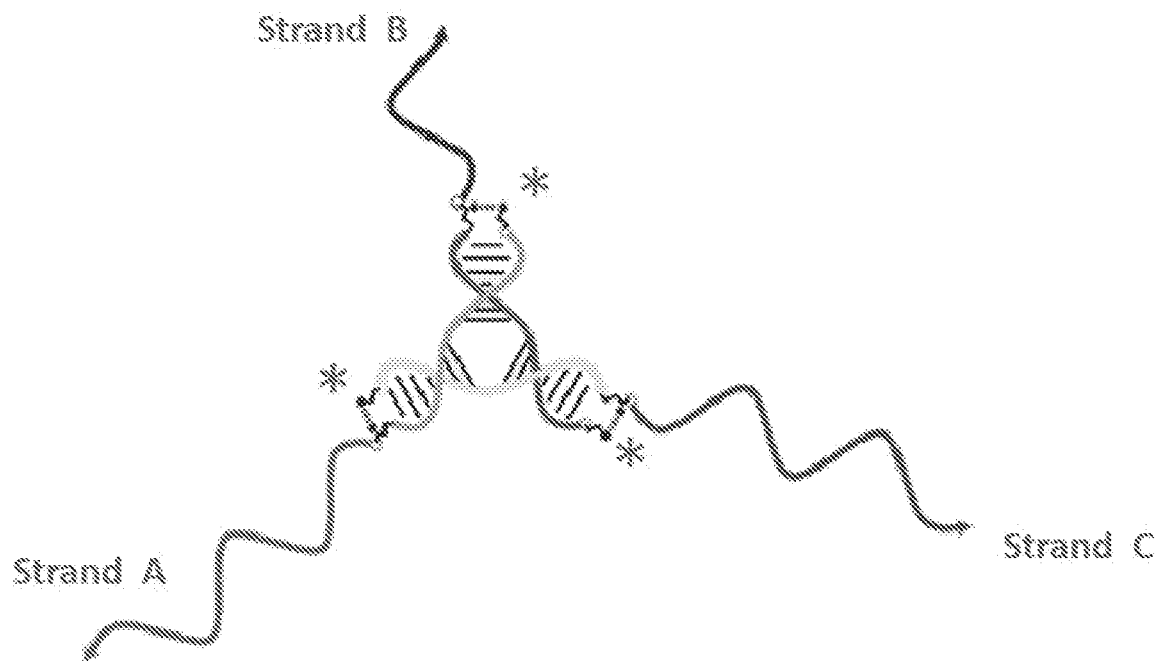
FIG. 3 illustrates an oligonucleotide three-way junction having an oligo-nucleotide core formed by three oligonucleotides, each two forming a complementary portion, and each oligonucleotide is attached to a single-stranded anchor strand (strand A, strand B, or strand C) at one end. The stars * denote the cross-linkers.
Figure 4:
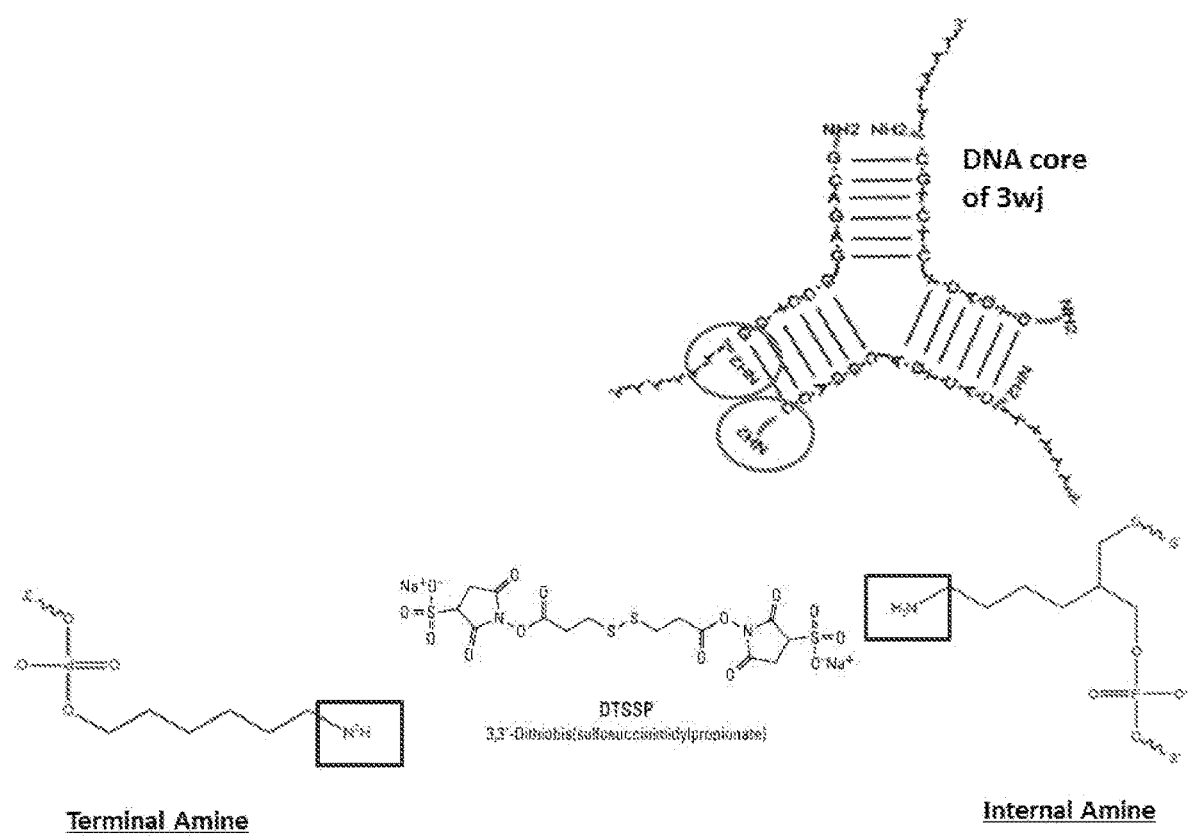
FIG. 4 shows an example of a DNA three-way junction core having three double-stranded arms, each arm having 6 base pairs. The extremity of each arm can be crosslinked by amine modifications of the terminal amine and the internal amine.

FIG. 3 shows an example of an oligonucleotide three-way junction. The oligonucleotide three-way junction disclosed herein comprises an oligonucleotide core formed by three oligonucleotides, wherein the two ends of each oligonucleotide complementarily bind to the two other oligonucleotides, and at least a portion of each end of each oligonucleotide complementarily binds at least a portion of one end of each of the two other oligonucleotides to form a double-stranded arm such that the three oligonucleotides form a three-way junction core having three double-stranded arms. In some embodiments, each oligonucleotide has a length of 10 nucleotides to 100 nucleotides. In some embodiments, each double-stranded arm comprises 15 base pairs, 14 base pairs, 13 base pairs, 12 base pairs, 11 base pairs, 10 base pairs, 9 base pairs, 8 base pairs, 7 base pairs, 6 base pairs, 5 base pairs, or 4 base pairs. The arms can have the same length or different lengths. FIG. 4 shows an example of a DNA three-way junction core having three double-stranded arms, each arm having 7 base pairs. The extremity of one or more arms can be crosslinked, for example, by amine modifications of the terminal amine and the internal amine. In this example, 3,3'-dithiobis(sulfosuccinimidylpropionate) (DTSSP) is used as the cross-linker.

Figure 5:
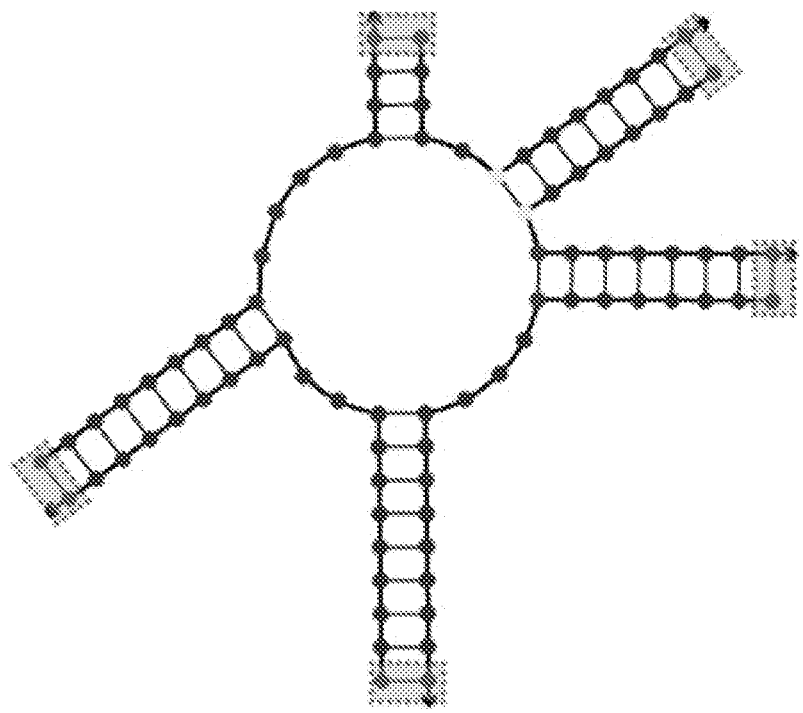
FIG. 5 shows an example of a 5-way junction with unequal length arms and non-base-paired bases in the center. Possible cross-linking positions are indicated by gray boxes. Cargo attachment sites are not shown.

As disclosed herein, a multi-way oligonucleotide junction can be formed by multiple oligonucleotides. Thus, an N-way oligonucleotide junction can be formed by incorporating N oligonucleotides, wherein N represents an integer from 3 to 15. FIG. 5 illustrates a 5-way junction core with unequal length arms and non-base-paired bases in the center. The number of the non-base-paired bases in the center is represented by $\beta$, which can be 1-50 bases. The size of the non-based paired center can be varied to provide desired instability of the junction such that the junction can dissociate faster once the cross-linker is cleaved upon entry into the cell. During storage or circulation, the cross-linker can provide sufficient stability of the junction. Possible cross-linking positions are indicated by gray boxes. Cargo attachment sites are not shown in this figure. In some embodiments, the multi-way oligonucleotide junction is an RNA junction in which the RNA sequences do not form base pairs. By varying $\beta$, the size of the non-base-paired center can be varied such that the RNA sequences can have tertiary interactions that set the arms at specific angles relative to each other. In some embodiments, the non-base-paired bases may be chemically modified to function as attachment sites for certain chemical linkers. In some embodiments, varying the size of the non-base-paired center can increase or decrease the melting temperature of the junction. In some embodiments, varying the size of the non-base-paired center provides a way to modulate the rotational flexibility of the arms relative to one another. Various designing software (e.g., Nupack, RNA Bricks[26]) can be used to calculate the algorithms of different non-based paired sequence and predict the secondary or tertiary structure of the junction.

Figure 6:
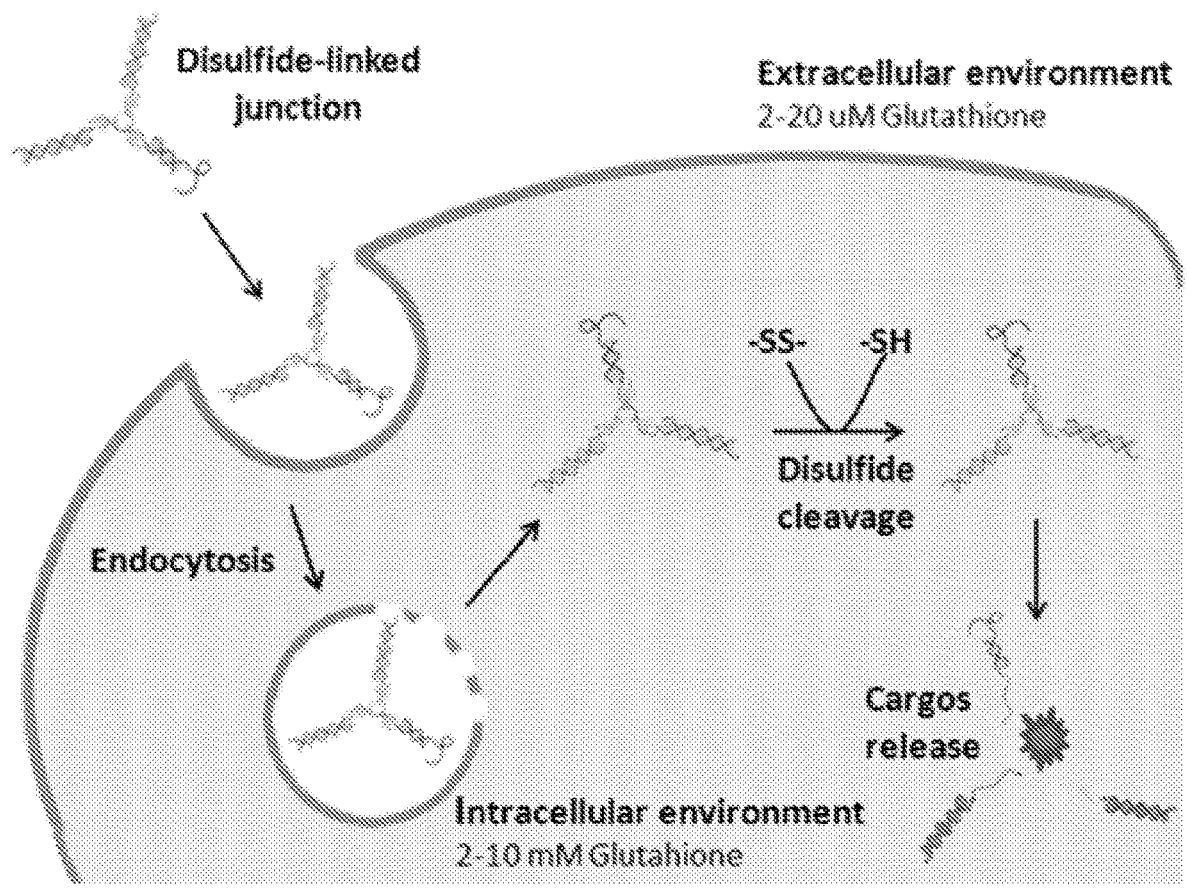
FIG. 6 (edited from a publication by Fleige et al. (10)) illustrates the process of a three-way oligonucleotide junction which is stable outside the cell dissolving inside the cell.

As a result of the small size of the junction core comprising the double-stranded arm(s), the oligonucleotide junctions disclosed herein is intrinsically unstable and dissociates spontaneously at body temperature (for example, 37° C.). In some embodiments, one or more arms are covalently cross-linked in the middle or at the extremity. The disulfide-bonds containing cross-linkers further stabilize the oligonucleotide junction outside the cell such that the oligonucleotide junction does not dissociate before being internalized into the cell. The cross-linker can contain chemical moieties that dissociate only under certain conditions, making the junction stable at a temperature between about 4° C. and about 37° C. For example, a disulfide-bond containing cross-linker can be used such that the crosslinked oligonucleotide three-way junction is stable in an extracellular environment where glutathione (GSH) is at a low concentration of 2-20 µM. Upon entry into an intracellular environment having GSH at a high concentration of 2-10 mM, reduction of disulfide-bond in the GSH rich environment facilitates dissociation of the oligonucleotide junction, thereby to release the cargo molecules carried by the oligonucleotide junction into the intracellular environment. The small size of the oligonucleotide junction core having a limited number of base pairs in each arm results in weak base paring between the complementary oligonucleotides, which allows easy dissociation of the junction once the cross-linkage is broken, further facilitates release of the cargo molecules into the intracellular environment. In some embodiments, the cross-linker is 3, 3'-dithiobis(sulfosuccinimidyl propionate) (DTSSP). DTSSP is a water-soluble cross-linker that contains sulfo NHS-ester ends at each extremity. Sulfo-NHS esters can react with primary amines added on the DNA strands (pH 7-9). The central disulfide bond is cleaved in the reducing glutathione-rich intracellular environment. Other cross-linkers also can be used, as detailed in this disclosure. For example, chemically labile linkers including acid-cleavable linkers (e.g., hydrazine, which remains stable at neutral pH during circulation and hydrolyses in the acidic cellular compartments), and reducible linkers including disulfide linkers (e.g., DTSSP, dimethyl dithiobispropionimidate (DTBP), and dithiobis(succinimidyl propionate) (DSP)) can be used. Various approaches are known in the art to reversibly cross-link oligonucleotides, including but not limited to disulfide crosslinking, crosslinking via click chemistry, photo-crosslinking, etc. FIG. 6 (edited from a publication by Fleige et al. (10)) illustrates the process of a three-way oligonucleotide junction stable outside the cell dissolving inside the cell.

Two or more oligonucleotides can be annealed to form the multi-way junction disclosed herein. The process of annealing allows at least a portion of each oligonucleotide to base-pair with at least a portion of another oligonucleotide. In some embodiments, annealing can be done by increasing the temperature to melt all existing secondary structures, and then cooling to form thermodynamically favored structures. In some embodiments, constant temperature binding can be performed such that at least a portion of each oligonucleotide can complementarily bind to a portion of another oligonucleotide at a certain temperature, e.g., at 4° C., 25° C., 37° C., 50° C., or 60° C. In some embodiments, annealing can be done by changing the salt concentration at a constant temperature. For example, annealing starts at 15° C., 0 M NaCl, and then progressively adding NaCl until reaching 1 M NaCl such that the oligonucleotides can be annealed.

Loading of Oligonucleotide Junctions

One or more cargo molecules can be loaded onto the oligonucleotide junction, and the same or different cargo molecules can be loaded onto each oligonucleotide junction. Thus, the oligonucleotide junction disclosed herein can be used for simultaneous, multifunctional delivery of various cargo molecules. In some embodiments, one end of an oligonucleotide of the junction is further attached to a single-stranded anchor strand. For a multi-way oligonucleotide junction, at least one single-stranded anchor strand can bind to an anchor pairing (AP) strand. The AP strand can comprise a cargo molecule (e.g., an siRNA or a DNA or RNA aptamer) or can be attached to a cargo molecule. Various cargo molecules can be delivered using the oligonucleotide junctions disclosed herein. In general, many small molecules and macromolecules can be conjugated to either or both of the anchor strand and the anchor pairing strand due to very versatile oligonucleotide attachment chemistry, including but not limited to amine-NHS ester conjugation, thiol conjugation, "click" linking, etc. Alternatively, small molecules or macromolecules can be directly attached to the junctions via linkers. In the embodiments where the cargo molecules are siRNAs, DNA or RNA aptamers, these cargo molecules can be loaded to the junctions by complementary binding to one or more anchor strands.

In some embodiments, at least one single-stranded anchor strand binds to a delivery ligand such that the oligonucleotide junction can target a specific type of cells. In some embodiments, the anchor strands are attached to the 3' end of each oligonucleotide of the junction. In other embodiments, the anchor strands are attached to the 5' end of each oligonucleotide of the junction.

In some embodiments, a cargo molecule can be attached to an oligonucleotide junction via a cleavable linker, such that the cargo molecule can be released upon entry into a cell. Various cleavable linkers can be used for the technology disclosed herein.[22-23] For example, chemically labile linkers including acid-cleavable linkers (e.g., hydrazine, which remains stable at neutral pH during circulation and hydrolyses in the acidic cellular compartments), and reducible linkers including disulfide linkers (e.g., DTSSP, dimethyl dithiobispropionimidate (DTBP), and dithiobis(succinimidyl propionate) (DSP)) can be used to attach a cargo molecule to an oligonucleotide junction. These reducible linkers provide sufficient stability when the cargo molecules loaded junctions are in circulation but the cargo molecules can easily dissociate in the presence of high concentration of reduced glutathione in intracellular compartments (2-10 μM) compared to extracellular environment (2-20 nM). In addition, reduced glutathione concentration is 1000-fold higher in some tumor cells than in normal cells such that the cargo molecules are more preferentially released in tumor cells.

In some embodiments, enzyme-cleavable linkers including peptide based linkers which are cleavable by intracellular proteases can be used for attachment of cargo molecules. Some examples include valine-citrulline dipeptide linker, phenylalanine-lysine dipeptide linker, etc.

Depending on the type of the cargo molecules, different techniques can be used to attach the cargo molecules onto the junctions. For example, amine reactive fluorophores, aldehyde reactive fluorophores, carboxylic acid reactive fluorophores, thiol reactive fluorophores, etc. are commercially available and can be readily attached to oligonucleotide junctions disclosed herein.

Figure 7A:
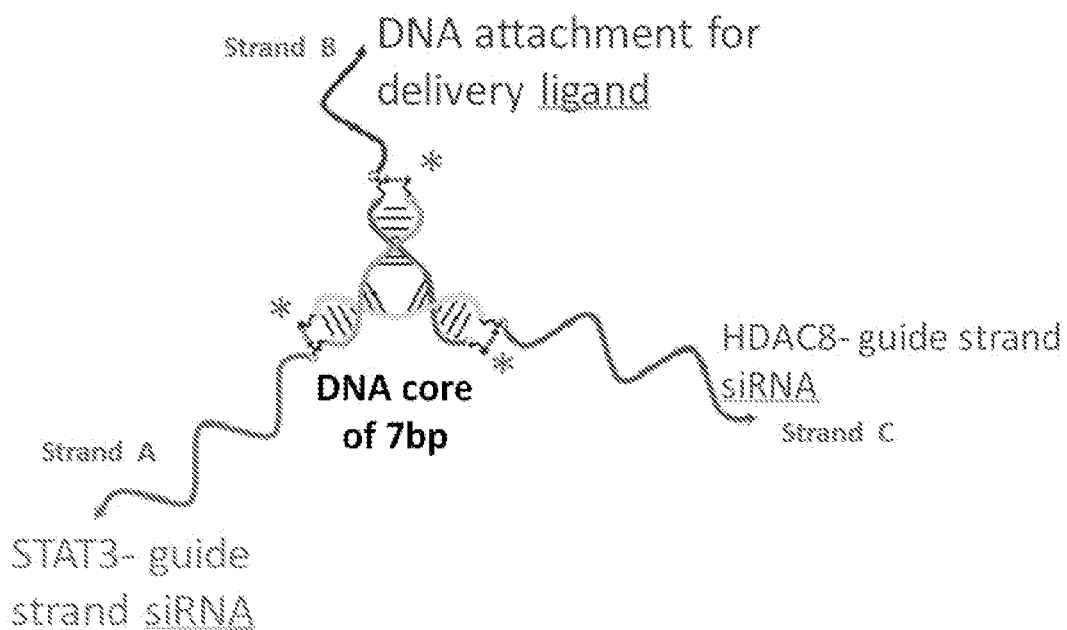
FIG. 7A shows an example of an unloaded three-way junction, where strands A, B, C are anchor strands for binding to cargo molecules and delivery ligand. In this illustrated example, the junction is used for delivery of different siRNAs and therefore, anchor Strand A and anchor Strand C are guide strands for STAT3 siRNA and HDAC8 siRNA, respectively, and anchor Strand B binds a delivery ligand.
Figure 7B:
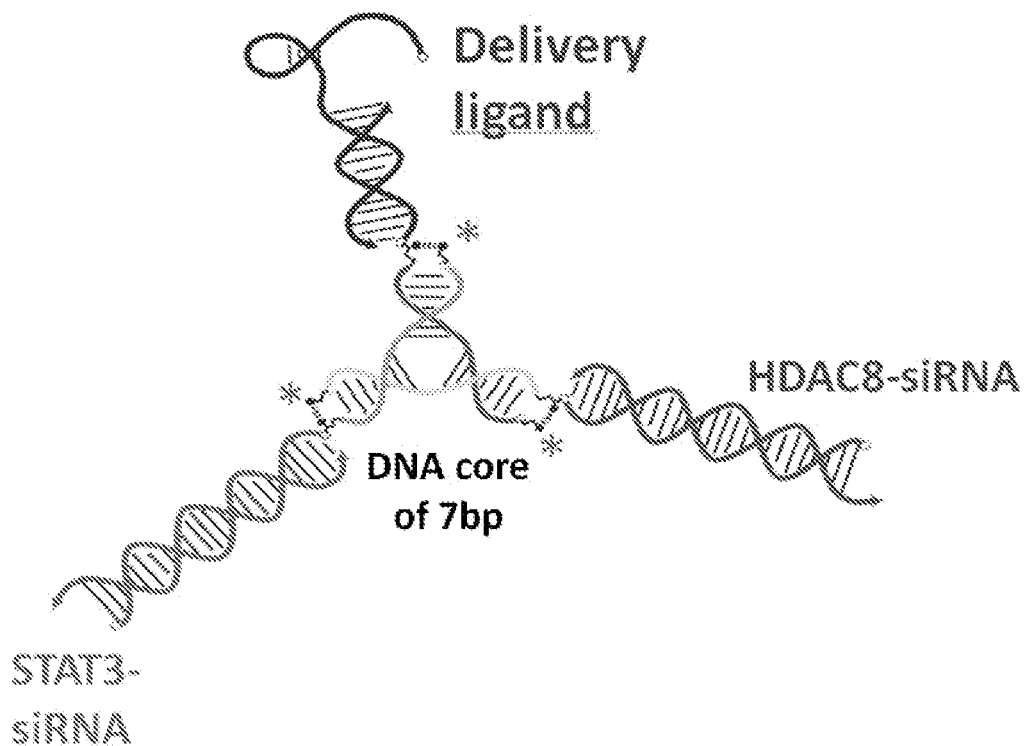
FIG. 7B shows an example of a three-way junction loaded with a delivery ligand, STAT3-siRNA and HDAC8-siRNA. * denotes the cross-linker.

The oligonucleotide junctions disclosed herein can achieve targeted delivery of multi-functional cargo molecules simultaneously. Using a three-way oligonucleotide junction as an example, one anchor strand can bind to a STAT3-siRNA, and another anchor strand can bind to an HDAC8-siRNA such that the loaded three-way junction simultaneously targets signal transducer and activator of transcription 3 (STAT3) and histone deacetylase 8 (HDAC8), which are known to promote tumorigenesis. The third anchor strand can bind to a delivery ligand that specifically targets the tumor cells. Such an oligonucleotide three-way junction loaded with STAT3-siRNA and HDAC8-siRNA can be used for treating Acute Myeloid Leukemia (AML). FIG. 7A shows an example of an unloaded three-way junction, and FIG. 7B shows an example of a three-way junction loaded with a delivery ligand, STAT3-siRNA and HDAC8-siRNA.

In some embodiments, either or both of the anchor strand and the anchor pairing strand are attached to a cargo molecule that is a drug or prodrug, a small molecule, a macromolecule (e.g., a protein or an antibody), a nanoparticle, a radioisotope, or a fluorophore such that the cargo molecule can be loaded to the junction via complementary binding between the anchor strand and the anchor pairing strand.

Chemical Modifications of Oligonucleotide Multi-Way Junction

The oligonucleotide multi-way junction disclosed herein can be further chemically modified. For example, some chemical modifications include but are not limited to amine modifications, alkyne modifications, phosphorothioate bond modification, 2'-O-methyl modification, $C_3$ spacer on the amine linkers.

Amines are the attachment sites for various cross-linkers. Various 5'-amino-modifiers are known in the art and commercially available. Additionally, thiol modification can be used to form disulfide linkages. "Click" chemistry is another approach used for synthesis of various conjugates with small molecules such as fluorores, biotins and other biomolecules to be attached to chemically modified oligonucleotide junctions. For example, the oligonucleotides can be alkyne modified such that they can be conjugated to a biomolecule labeled with an active azide group in the presence of a catalyst (e.g., copper). Alternatively, the oligonucleotides can be modified to add an azide group such that they can be conjugated to a biomolecule containing alkynes in the presence of a catalyst (e.g., copper). Other "click" reactions may not require the presence of a catalyst. For example, the oligonucleotides can be modified to add an azide group or a dibenzo-cyclooctyne (DBCO) structure such that they can be conjugated to a cargo molecule modified by DBCO or azide via reactions between DBCO and azide.

Phosphorothioate bond modification is an oligonucleotide modification that replaces a phosphodiester bond between the bases in a standard oligonucleotide linkage with a phosphorothioate bond, which renders the modified oligonucleotide more resistant to nuclease degradation. In some embodiments, one or more phosphorothioate bonds are introduced to one or more oligonucleotides of the three-way junction. In some embodiments, one or more phosphorothioate bonds are introduced between the nucleotides at the 5' end of the oligonucleotides. In some embodiments, one or more phosphorothioate bonds are introduced between the nucleotides at the 3' end of the oligonucleotides. In some embodiments, one or more phosphorothioate bonds are introduced internally. Phosphorothioate bonds can be used at any location of the oligonucleotides in the junction or in the cargo molecule to improve stability and pharmacokinetics.

In some embodiments, 2'-O-methyl modification can be used to modify small RNAs, e.g., antisense oligos, to increase stability and binding affinity to the targets. Various modified oligos known in the art can be used in the technology disclosed herein.[24, 25]

In some embodiments, non-oligonucleotide spacers such as $C_3$ spacer or Peg can be added on the amine linkers for attachment of fluorophores or other small molecule drugs.

Figure 8:
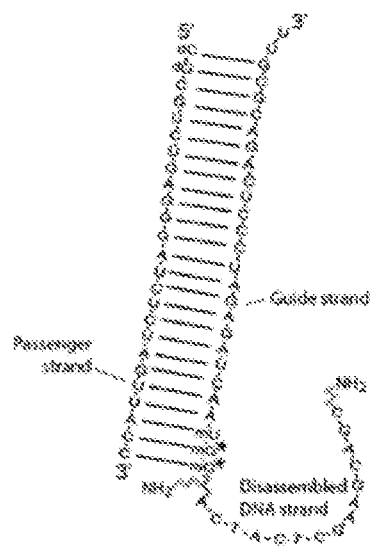
FIG. 8 shows a released synthetic dicer substrate that is the projected result of the dissociation of an oligonucleotide junction. The passenger strand can be, for example, an siRNA, and the single-stranded overhang represents the component strand of the junction which has been released.

As shown in FIG. 8, once an oligonucleotide junction (using a synthetic dicer substrate as an example) is released and dissociates in a cell, the single-stranded DNA overhang is released from the component oligonucleotide of the junction. The presence of a single-stranded oligonucleotide can lead to undesired degradation of the junction carrying therapeutic cargo molecule, e.g., an siRNA, by exonuclease activity. The chemical modifications disclosed herein can control exonuclease degradation so that the single-stranded overhang can be removed by the cell itself without degradation of the therapeutic cargo molecule.

Optimization of the Yield of Oligonucleotide Multi-Way Junctions

By the standard annealing and crosslinking procedures, about 25% of an oligonucleotide junction can be produced. However, optimizing the reaction conditions can result in a significantly improved synthesis efficiency, increasing the yield of the oligonucleotide junction from about 25% to up to about 75%. The reaction conditions that can be optimized include, for example, the concentration of the cross-linker, the choice of a specific crosslinking buffer, the salt concentrations and/or pH of all buffers used in the reactions, and the concentrations of the single-stranded oligonucleotides to be attached to the three-way junction (e.g., the concentrations of the anchor strands).

Nanostructures

Figure 9:
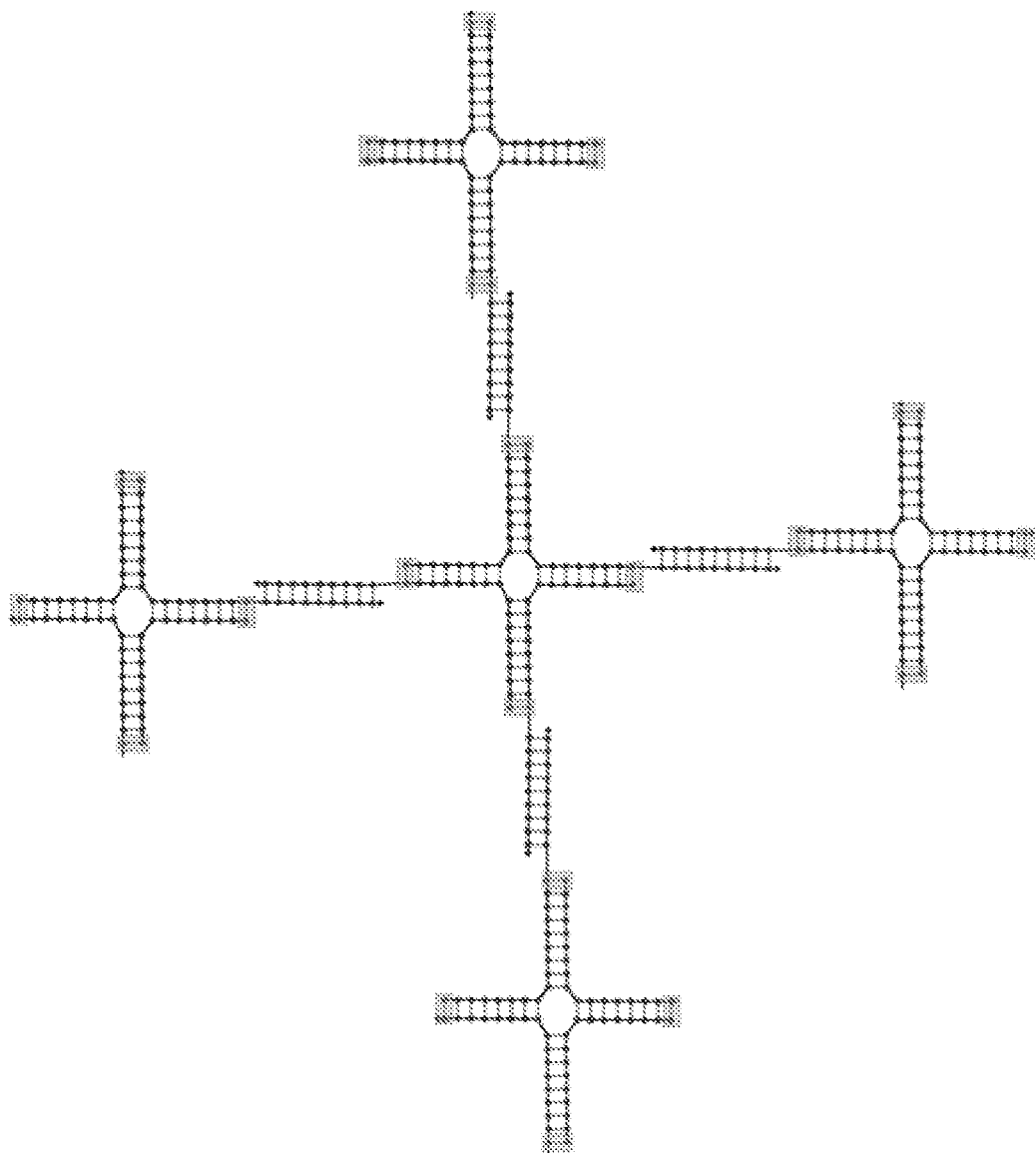
FIG. 9 illustrates an example of a nanostructure formed by 4-way oligonucleotide junctions in a branching network. The junctions are connected by base-pairing. The gray boxes indicate possible crosslinking positions.
Figure 10:
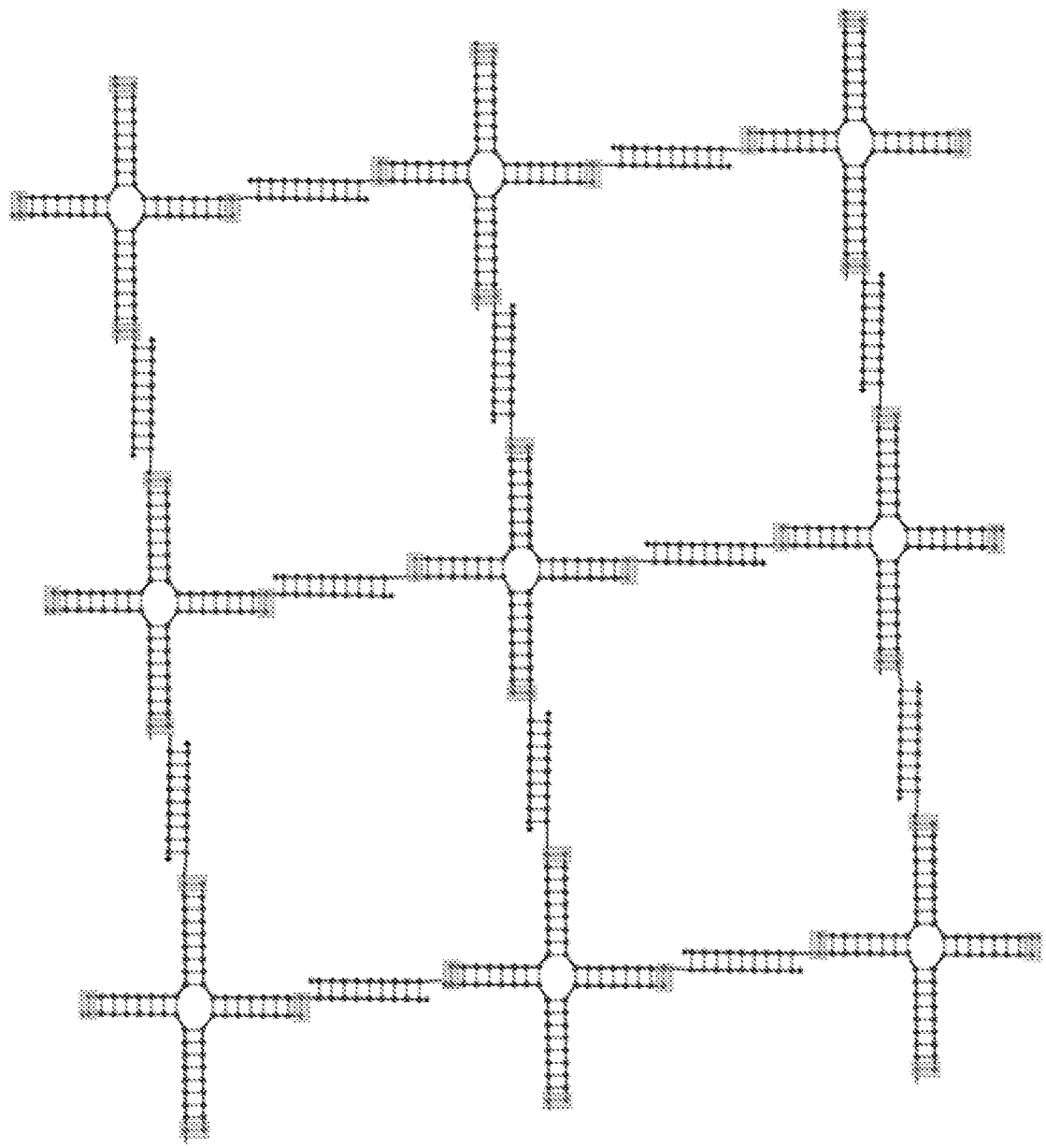
FIG. 10 illustrates another example of a nanostructure formed by 4-way oligonucleotide junctions in a 2D array. The junctions are connected by base-pairing. The gray boxes indicate possible crosslinking positions.

Multi-way oligonucleotide junctions disclosed herein can be linked, attached or conjugated to each other to form larger nanostructures. FIG. 9 demonstrates a nanostructure formed by 4-way junctions, however, any N-way junction can be incorporated into a nanostructure. As shown in FIG. 9, each of the outer junctions can have additional attached oligonucleotide junctions or structures to form a multi-generation dendrimer. The 4-way junctions can be linked in different configurations. In another example shown in FIG. 10, the 4-way junctions can form a 2D array.

Figure 11A:
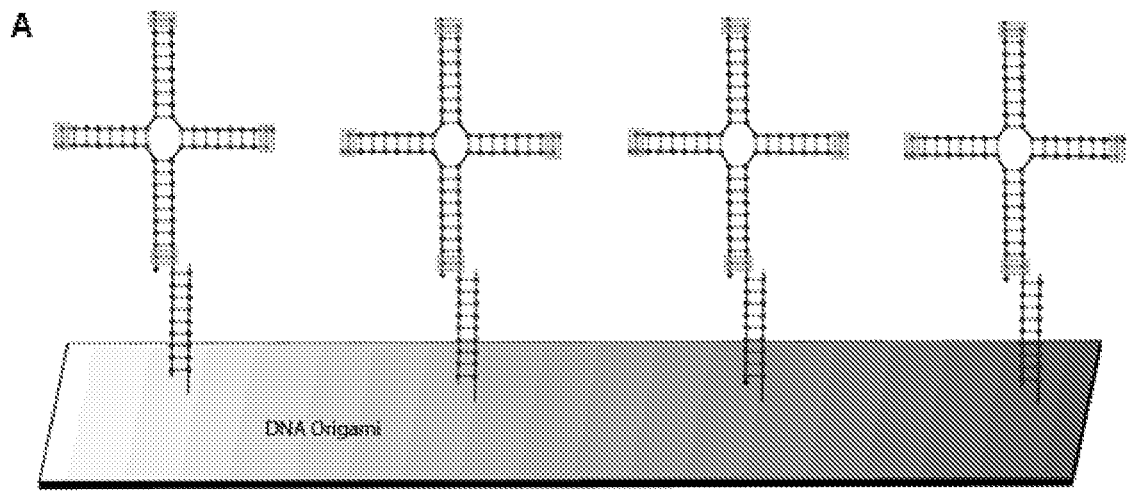
FIG. 11A shows an example of multiple 4-way junctions attached to a DNA origami.
Figure 11B:
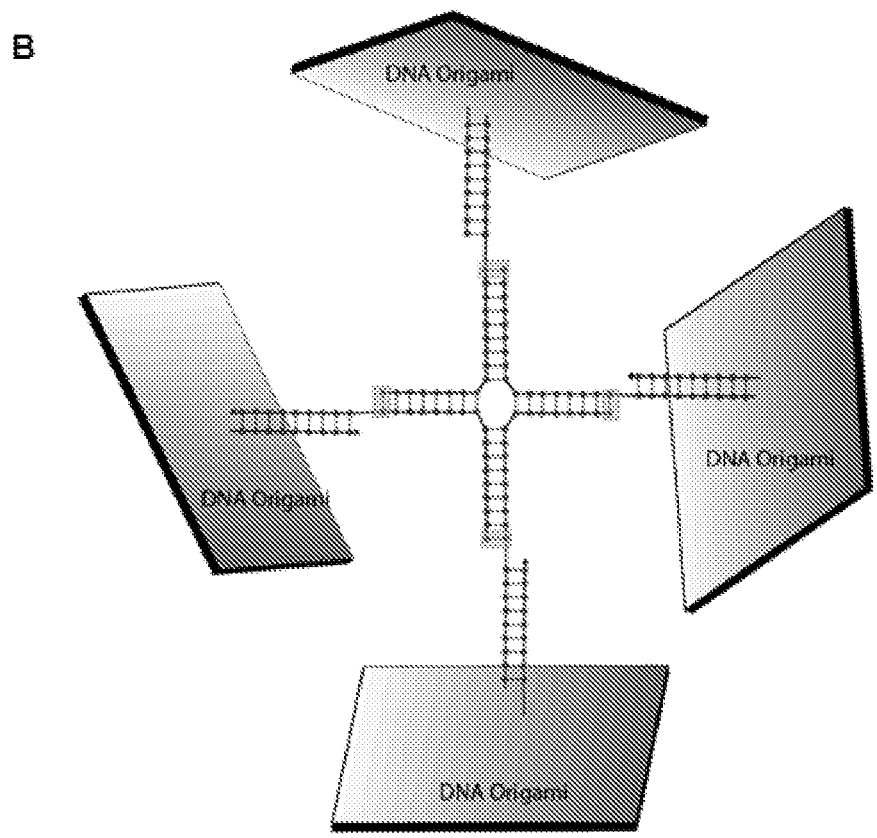
FIG. 11B shows an example of a single 4-way junction functioning as a "hub" and attached to multiple DNA origamis.
Figure 12:
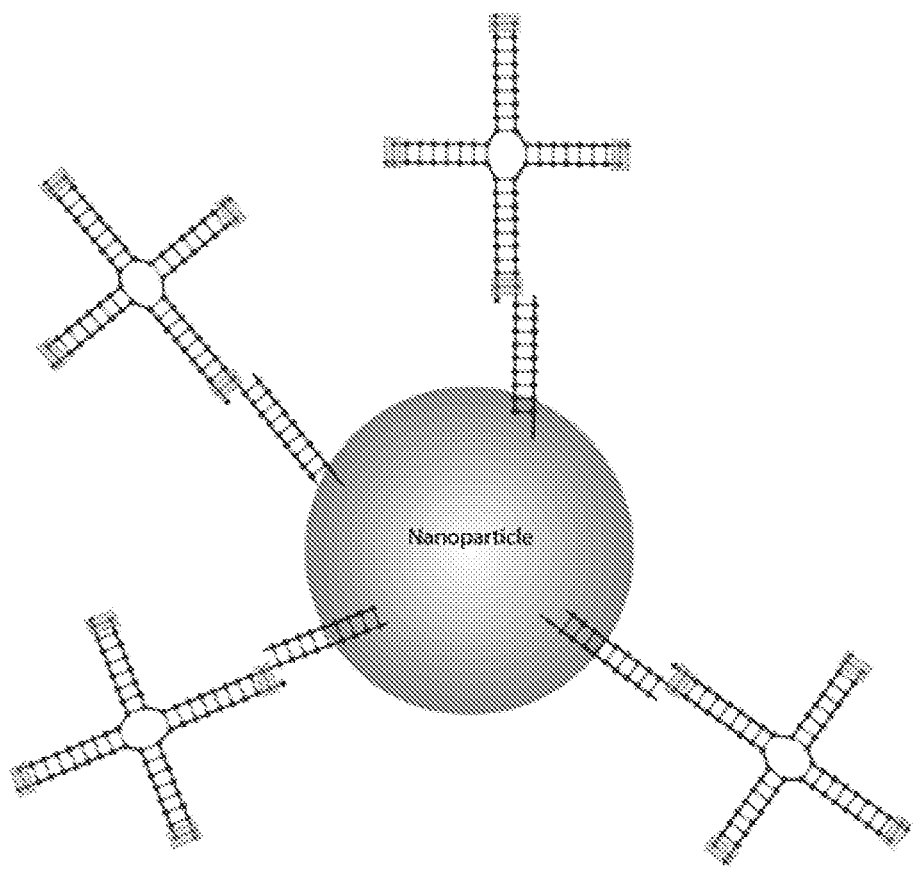
FIG. 12 shows an example of multiple 4-way junctions attached to a nanoparticle.
Figure 13:
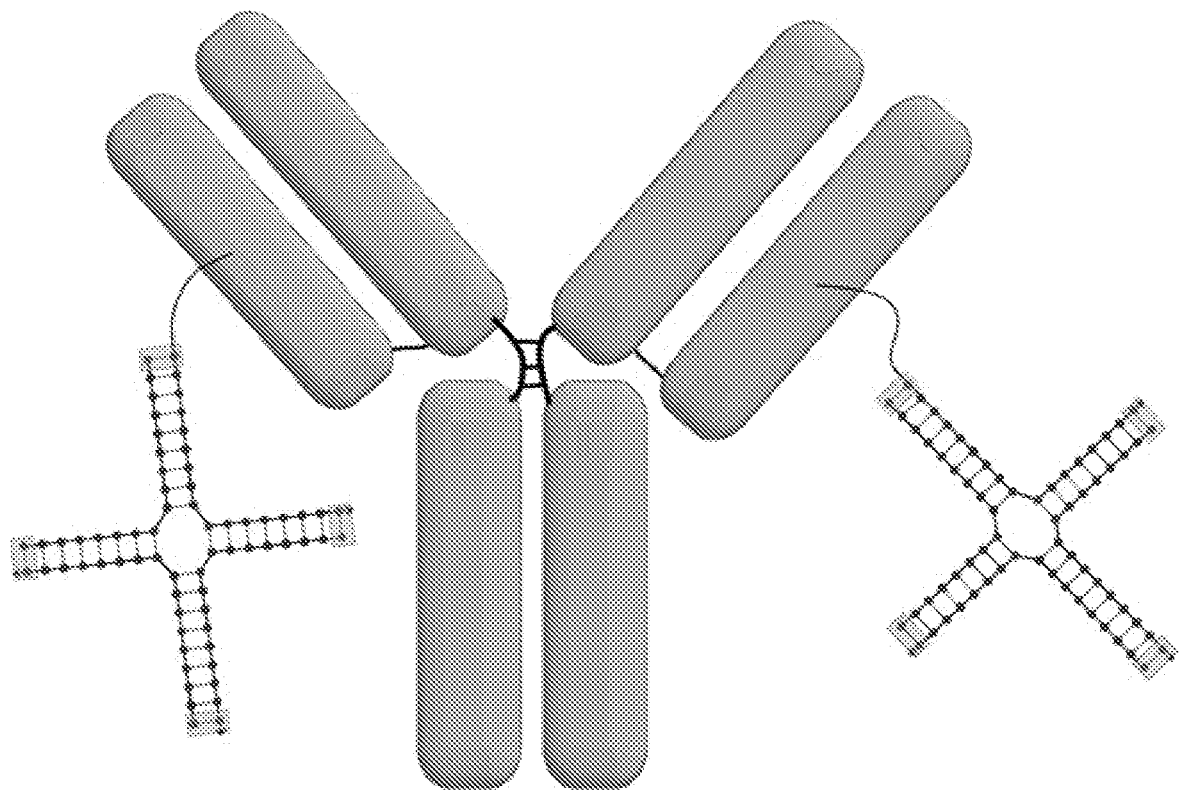
FIG. 13 shows an example of multiple 4-way junctions attached to an antibody.

Additionally, multiple oligonucleotide junctions can be attached to another type of oligonucleotide nanostructure or, alternatively, a single oligonucleotide junction can be attached to multiple other oligonucleotide nanostructures. As shown in FIGS. 11A and 11B, multiple 4-way junctions can be attached to one DNA origami structure (11A), or a single 4-way junction can be attached to multiple DNA origami structures (11B). Various nanostructures, macromolecules, and biomolecules can be delivered by the multi-way oligonucleotide junctions disclosed herein. For example, FIG. 12 illustrates that multiple 4-way junctions can be attached to a nanoparticle, and FIG. 13 illustrates that multiple 4-way junctions can be attached to an antibody for delivery into cells. One or more arms can be attached to one or more delivery ligand for targeted delivery to desired cell type.

Figure 17:
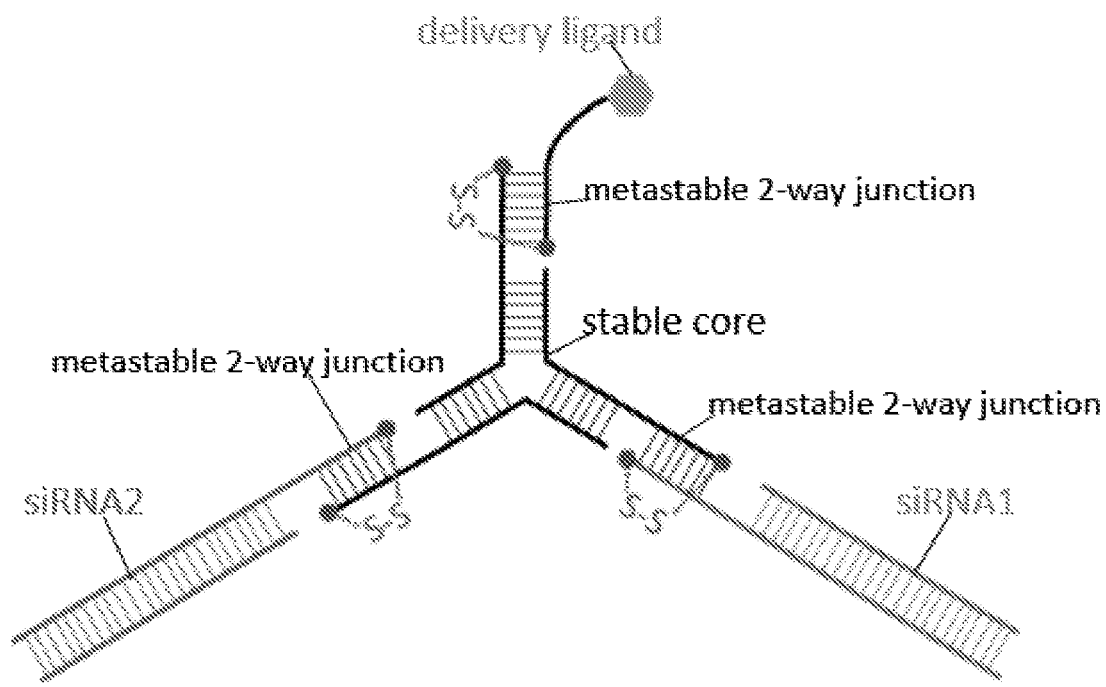
FIG. 17 illustrates the design of a nanostructure including a three-way junction core, with each arm attached to a two-way junction. The other end of each of the two-way junctions can be attached to a cargo molecule such as an siRNA or a delivery ligand targeting a cell.

As disclosed herein, a nanostructure can be formed by attaching two or more junctions to each other. For example, two, three, four, five, six, or more junctions are attached to each other to form a nanostructure. In some embodiments, disclosed herein is a nanostructure comprising a core of a three-way, four-way, five-way junction, or six-way junction, and a two-way junction attached to each arm of the three-way, four-way, or five-way junction core. In some embodiments, the core can be a multi-way junction having more than six arms, with each arm attached to a two-way junction, and a cargo molecule or delivery ligand loaded to the other end of the two-way junction not attached to the core. As illustrated in FIG. 17, a nanostructure disclosed herein is formed by a three-way junction core, and three two-way junctions, each two-way junction attached to an arm of the three-way junction core. In alternative designs, the core of such a nanostructure can be a four-way, five-way, six-way, seven-way, or eight-way junction, and each of the two-way junctions can have one end attached to the four-way, five-way, six-way, seven-way, or eight-way junction core and the other end attached to a cargo molecule such as an siRNA or a delivery ligand targeting a cell. In some embodiments, the multi-way junction core of the nanostructure is stabilized by chemical modifications such as 2'-O-methyl modification and lock nucleic acid bases (LNA).

The nanostructures disclosed in the foregoing paragraph has a core that remains stable in both of the extracellular and the intracellular environment. As illustrated in FIG. 18, in the intracellular environment, the siRNAs are released by the dissociation of the metastable two-way junctions that serve as attachment points to the three-way junction core. The dissociation of the two-way junction occurs due to the cleavage of the disulfide bonds stabilizing the junction in the high glutathione concentration environment of the cytosol.

Figure 20:
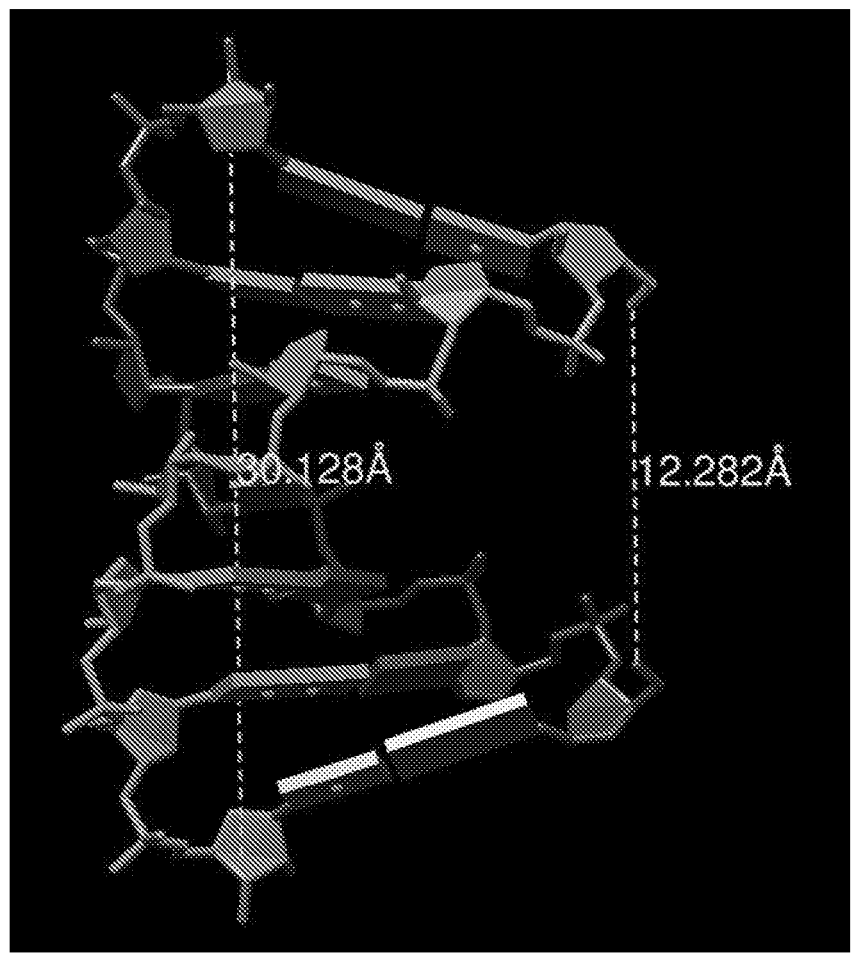
FIG. 20 illustrates the molecular modeling of a 7 base-pair two-way junction, where the 5' ends of the component strands are 12.28 Angstroms apart, and the 3' ends are 30.13 Angstroms apart. Thus, the 5' ends can be good attachment points for a cleavable cross-linker.

As discussed above, the junctions can be modified by cleavable cross-linkers. Using a two-way junction as an example, FIG. 20 illustrates that by varying the length of the two-way junction, the distance between the 5' ends can be optimized to become good attachment points for a cleavable cross-linker.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLES

Example 1: Dicer Processing of Synthetic Dicer Substrate

In this experiment, synthetic Dicer substrates with different secondary structures adjacent to the 25 base-pair RNA duplex were tested in human HCT116 colon cancer cells for efficiency of Dicer processing.

Each construct shown was transfected into HCT116 cells using Lipofectamine 2000 according to the manufacturer's instructions. 24 hours later, the cells were lysed, the total cellular RNA was extracted. This RNA material was run through a denaturing polyacrylamide gel, transferred to a blotting paper, and probed by radioactively labeled oligonucleotide probes complementary to the anchor strand of the Dicer substrate.

As shown in FIG. 1, the Northern blot results demonstrate that constructs that did not have additional secondary structure attached near the 5' of the guide strand (the ones in the boxes) were efficiently processed by Dicer, leading to appearance of the small band at the bottom of the gel, which was from the cleaved guide strand. In contrast, those that did have additional secondary structure, showed no cleavage of the guide strand, meaning that they had not been efficiently processed by Dicer.

This experiment shows that additional RNA secondary structures attached to Dicer substrates and possibly other RNAi substrates could compromise the efficiency of enzymatic processing of the substrates, and RNAi loading, thereby compromising their therapeutic activity. This provides motivation for using "metastable" junctions that can dissociate in intracellular or other treatment pertinent biological environment to increase efficiency of processing and therefore, the biological activity.

Example 2: Assembly and Loading of Oligonucleotide Three-Way Junction

In a first annealing step, three oligonucleotides were annealed in the presence of NaCl in a thermocycler over a period of about 75 minutes at three temperatures: heating to 85° C. for 30 seconds followed by a decrease in the temperature at a rate of 1° C./s, annealing at 60° C. for 1 minute, and slowly cooling down to 10° C. at a rate of 0.02° C./s. A three-way junction was assembled after the first annealing step. Next, the assembled three-way junction was crosslinked in the presence of 5 mM DTSSP in HEPES buffer supplemented with 50 mM $CaCl_2$) at 5° C. for 24 hours. An alternative crosslinking buffer containing salt (NaCl, KCl), divalent ions ($Mg^{2+}$, $Ca^{2+}$) having a pH between 7 and 9 was also used. The cross-linked three-way junction was then mixed with the delivery ligand and passenger strands in a second anneal step such that the delivery ligand and passenger strands bound to the ligand attachment strand and the guide strands, respectively. The second anneal step was conducted over a period of about 60 minutes at three temperatures: heating to 75° C. for 30 seconds followed by a decrease in the temperature at a rate of 1° C./s, annealing at 60° C. for 1 minute, and slowly cooling down to 37° C. at a rate of 0.02° C./s.

Example 3: Optimizing the Yield of the Three-Way Junction

Figures 14A, 14B:
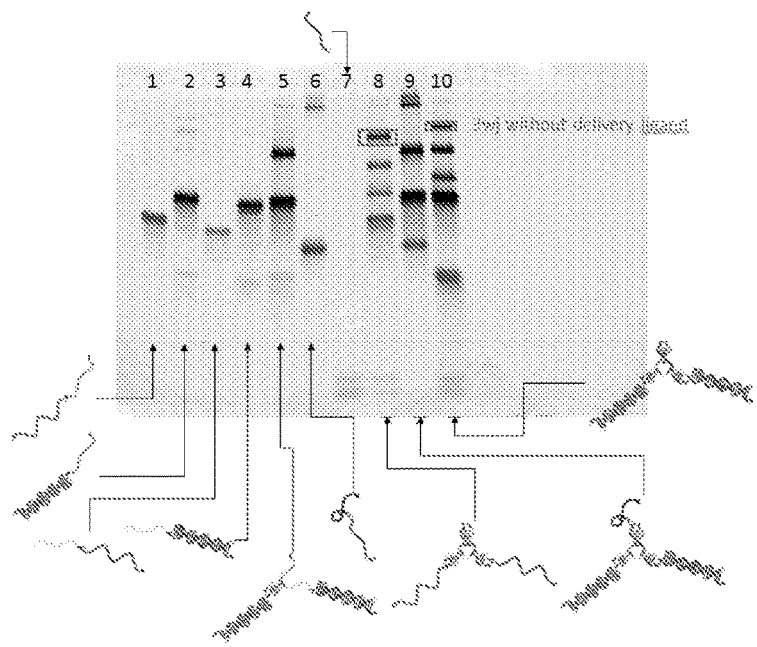
FIG. 14A shows urea-denaturing PAGE electrophoresis analysis of the yield of three-way junction before optimizing the reaction conditions.
FIG. 14B shows urea-denaturing PAGE electrophoresis analysis of the yield of three-way junction after optimizing various reaction conditions. * denotes a DNA core without cargo molecules.

This example demonstrates that the yield of the three-way junction was increased by 3-fold when the crosslinking and annealing reaction conditions were further optimized. As shown in FIG. 14A, the standard procedure resulted in a yield of about 25% three-way junction. As shown in FIG. 14B, the yield of the three-way junction was improved by optimizing various reaction conditions, such as the concentration of the cross-linker, the choice of the crosslinking buffer, the salt concentration and the pH of the reaction buffers, and the reactant (e.g., the anchor strand) concentration. The combination of these optimized reaction conditions resulted in an improved synthesis efficiency of about 75%.

Example 4: Design and Construction of a 6-Way Oligonucleotide Junction

This example illustrates the design process of a 6-way junction in which several arms are stabilized via reversible crosslinking. Under intracellular conditions, a portion of this 6-way junction dissociates to release cargo molecules for their therapeutic functions.

Figure 15:
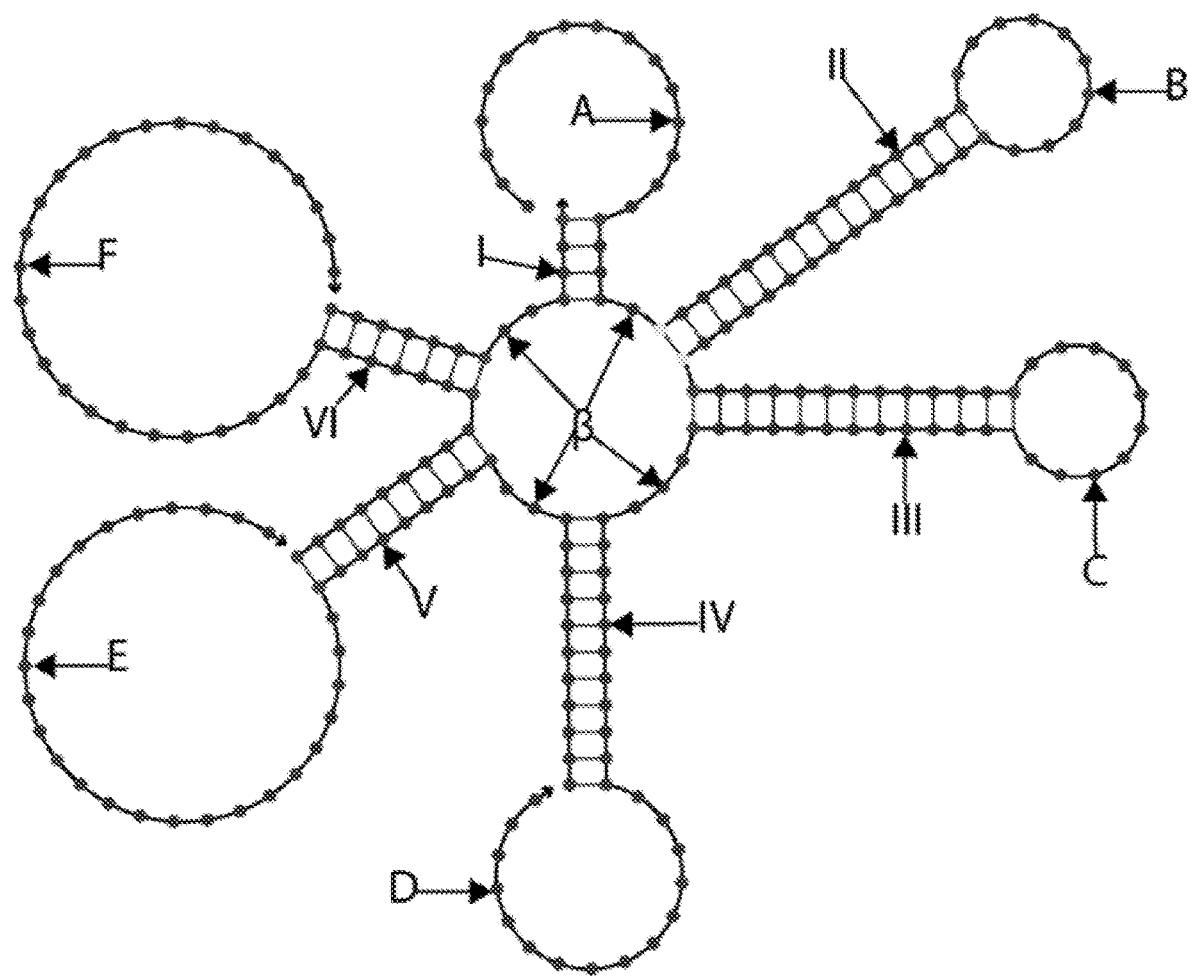
FIG. 15 illustrates the design of a 6-way junction, where unequal length arms I-VI and single-stranded domains (A-F) attached to the arms are shown. β represents the number of unpaired bases in the center, which can be varied.

FIG. 15 illustrates the design of a 6-way oligonucleotide junction having 6 unequal length arms: arm I with 4 base pairs, arms II and III each with 15 base pairs, arm IV with 11 base pairs, arm V with 9 base pairs, and arm VI with 7 base pairs. Different arm lengths can be configured to, for example, achieve the desired Tm for the structure, or, in the case of arms II and III, for example, be at specific lengths for projecting different ligands target specific binding in targeted drug delivery.

The 6-way junction also has multiple domains with no canonical Watson-Crick base-pairing. For example, domain A is a 15-base domain designed to be an adapter for binding an additional ligand, domain B is a 10-base terminal loop, e.g., an aptamer, domain C is another 10-base terminal loop, e.g., a second aptamer, domain D is a 15-base adaptor for binding an additional ligand, domain E is a 27-base guide strand for binding a cargo molecule, e.g., an siRNA, and domain F is another 27-base guide strand for binding a second cargo molecule, e.g., a second siRNA. Domains B and C together, for example, can be used for bivalent binding to one or two different cell surface receptors. The cargo molecules (e.g. siRNAs) can be the same or different.

Automated design applications such as NUPACK (http://nupack.org), a web-based application, can be used to optimized the design of the 6-way junction. The NUPACK application[11], analysis algorithms[12-14] and design algorithms[15-18] were described in prior publications.

In this example, a 6-way DNA junction was designed with the temperature set at 15° C., the number of designs set at 10, and the ion concentrations set at 1.0 μm of sodium. The sequences of the siRNA guide strands in two of the overhangs were also included in the algorithm. Additionally, undesirable sequences such as GGG and CCC were avoided to prevent formation of G quadraplexes, and WWWW (representing A/T or A/U base pairing) was also avoided to prevent A/T or A/U rich base pairing resulting in unstable regions. A set of strand sequences was selected based on low errors and no obviously problematic domains from the NUPACK design results:

```
Strand 1, 5'->3' (SEQ ID NO: 1):
TTTCTTTCATCTACCACCGCATCGGAAGTGCCGGACGCCTTTCCTAGTC

CGGCACTTCCGAGCTGCGGTGACTGAAGAGCAAGACAGTCACCGCAGCC

ATGTTACGGCGACATCATTCACCTCACT

Strand 2, 5'->3' (SEQ ID NO: 2):
GTCGCCGTAACTACAATCAACGCCACCTCTCCACCTCCAAACCACCAAC Strand 3, 5'->3':
CGTTGATTGCTCGCCGACTTTCCACCACCTCCACTCTACACAC Strand 4, 5'->3' (SEQ ID NO: 3):
CGGCGAGTAGCGG
```

The results showed that 99% of the strands were expected to assemble into the correct complex at 15° C., 1 μM strand concentration for each strand and 1 M NaCl concentration.

Next, the stability of the 6-way junction design in the cellular environment under nominal expected conditions were analyzed using NUPACK. The test conditions were varied according to the conditions under which disassembly was desired, for example, temperature at 37° C., strand concentration at 1 nM for each strand, NaCl concentration at 200 mM, MgCl$_2$ concentration at 2 mM. These conditions led to almost complete disassembly of the 6-way junction, indicating that this design of the 6-way junction is acceptable.

For carrying siRNAs, the guide strand portions of the siRNA can be changed to RNA oligonucleotides. In addition, some nucleotides have to be changed into chemically modified oligonucleotides. Currently, there are no computational tools that are capable of predicting the secondary structure of a mixed RNA/DNA chimera structure with modified nucleotides. However, a DNA design that is able to assemble into the designed nanostructure with high yield can have portions changed into RNA without compromising the assembly. Further modifications can be made taking into consideration that RNA:RNA base-pairs are more thermodynamically stable than RNA:DNA base-pairs.

The secondary structure of the design of the 6-way junction for RNA strands of the identical sequence was analyzed at a temperature of 15° C. or 37° C., strand concentration at 1 μM or 1 nM for each strand, and NaCl concentration at 1 M. The sequence for each strand is as follows:

```
Strand 1, 5'->3' (SEQ ID NO: 4):
UUUCUUUCAUCUACCACCGCAUCGGAAGUGCCGGACGCCUUUCCUAGUC

CGGCACUUCCGAGCUGCGGUGACUGAAGAGCAAGACAGUCACCGCAGCC

AUGUUACGGCGACAUCAUUCACCUCACU

Strand 2, 5'->3' (SEQ ID NO: 5):
GUCGCCGUAACUACAAUCAACGCCACCUCUCCACCUCCAAACCACCAAC Strand 3, 5'->3' (SEQ ID NO: 6):
CGUUGAUUGCUCGCCGACUUUCCACCACCUCCACUCUACACAC Strand 4, 5'->3' (SEQ ID NO: 7):
CGGCGAGUAGCGG
```

Results at the putative assembly condition of 15° C. and 1 μM strand concentration showed 98% assembly yield for the RNA version of the junction. Results at the putative intracellular condition of 37° C. and 1 nM strand concentration showed likely disassembly. Thus, the designed sequences can be used either for a DNA based junction or an RNA based junction.

Figure 16:
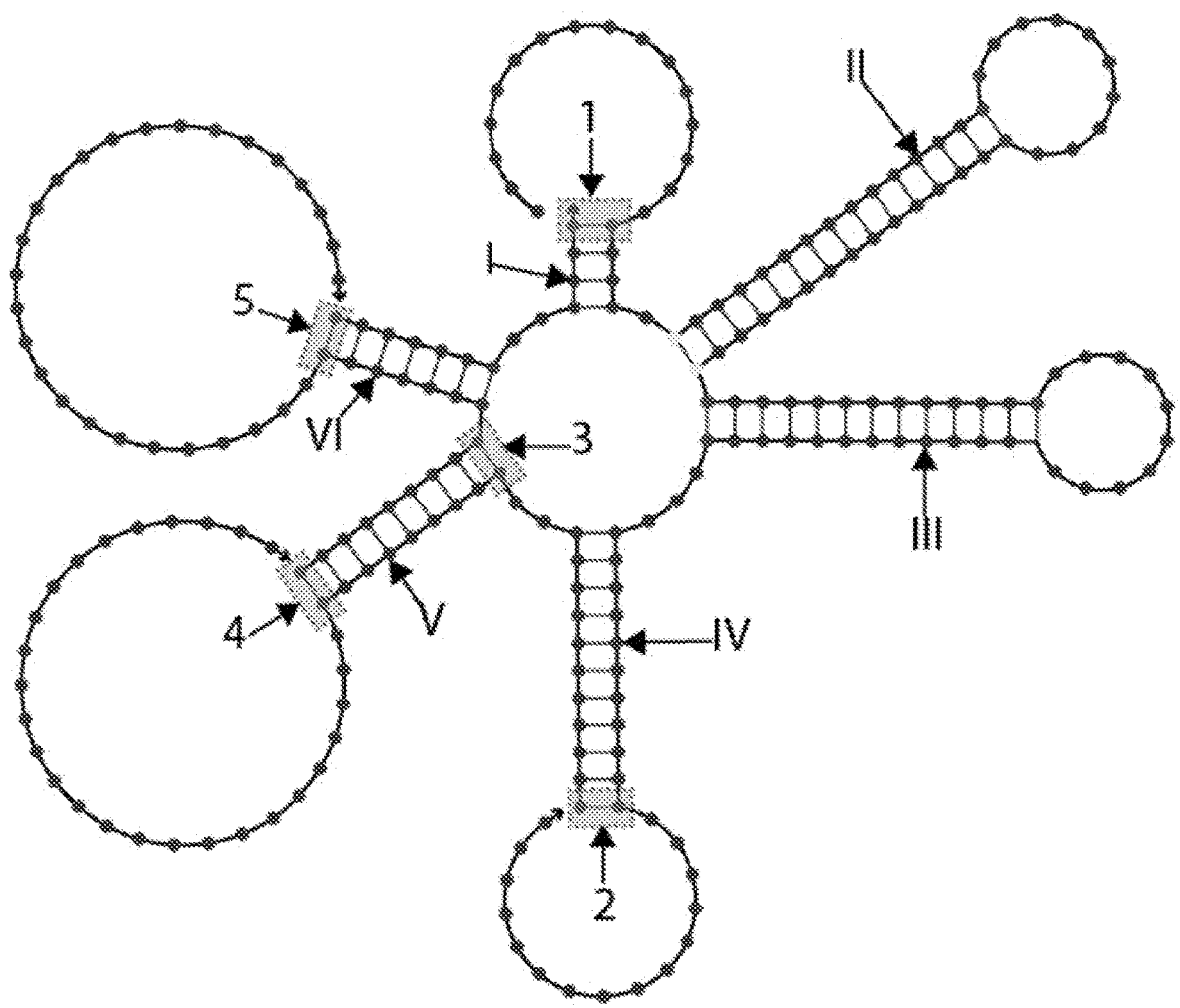
FIG. 16 illustrates the design of the 6-way junction of FIG. 15, with unequal length arms I-VI and possible cross-linking sites 1-5.

After sequence design and analysis, cross-linkers can be placed at selected positions on the junction, as shown in FIG. 16. For example, arms II and III are internal secondary structures in strands designed for carrying ligands and aptamers that help in vivo delivery. Therefore, arms II and III are not crosslinked. Cross-linking sites 1-5 for arms I, IV, V and VI can be placed as shown as the gray boxes in FIG. 16.

When considering the placement of locations for cross-linkers, it's necessary to consider the distance between neighboring cross-linkers. More than one cross-linker can be placed in each arm, e.g., cross-linking sites 3 and 4 are both located on arm V.

Cross-linking sites should be spaced so that a cross-linker binds unambiguously to a specific pair of attachment sites. For example, at the positions indicated in FIG. 16, cross-linking sites 3 and 4 are spaced by 8 base-pairs. This means that these two sites are spaced ~2.7 nm apart for a DNA arm and 2 nm apart for an RNA arm. When a cross-linker longer than 2 nm is used, it is possible that the cross-linker intended to crosslink the bases at site 4 erroneously links one base at site 3 and another base at site 4. This erroneous cross-linkage would decrease control over the crosslinked configuration of the junction. Thus, the crosslinking sites should be spaced at a greater distance than the length of the cross-linker molecule so that crosslinking of the specific bases is achieved.

Several methods can be used to assess whether there is sufficient distance between the crosslinking sites. For example, the crosslinking sites should be placed at a distance greater than the maximum extended length of the cross-linker molecule; use molecular simulations to determine whether a particular cross-linker can reach from one cross-linking site to another crosslinking site; or experimentally generate a particular oligonucleotide junction, check the pattern of crosslinking by cutting the junction using nucleases to analyze the pattern of fragments on denaturing gels or using mass spectrometry, and deduce whether crosslinking is specific to each site as desired or there is random crosslinking between different sites.

Random crosslinking can be reduced by varying cross-linking sites or adjusting attachment chemistry. The same attachment chemistry or different attachment chemistries can be used for all crosslinking sites. For example, if two crosslinking sites are too closely spaced, amine attachment at one site and click attachment at the other site can be used to reduce random crosslinking. This would allow well controlled cross-linkage at both sites even if they are very closely spaced.

After determining the crosslinking sites, additional chemical modifications can be made to different domains of the 6-way junction according to the functions of different domains. For example, loops F and E can be changed to RNA oligonucleotides and chemically modified RNA base analogues[19,20] are used to improve function of the cargo siRNA. Furthermore, the aptamer domains in loops B and C can utilize chemically modified DNA base analogues[21] to improve ligand binding as appropriate.

If a desired structure, assembly yield, or cross-linker configuration is not achieved, many design elements can be adjusted to optimize the production of the 6-way junction. For example, the sequence composition and arm length can be adjusted to change thermodynamic stability; the crosslinking sites can be moved to achieve better crosslinking efficiency and control; the crosslinking attachment chemistry can be changed to improve crosslinking yield; and the chemical modifications can be changed.

Example 5 Synthesis of Nanostructure

This example demonstrates the synthesis process of a nanostructure illustrated in FIG. 19. To form a three-way junction core, the three component strands of the three-way junction core were reacted with sulfo-NHS-ester-DBCO linkers to attach DBCO to primary amines at the ends of the strands. Excess linkers were removed by ethanol precipitation. And then the DBCO-labeled strands were base-paired in the thermocycler resulting in a three-way junction core.

Separately, the delivery ligand and the siRNAs were each reacted with sulfo-NHS-ester-DBCO linker in step 1, followed by ethanol precipitation to remove excess linkers, and then linking to Azide-disulfide linker. Subsequently, the delivery ligand and siRNAs with linkers added were attached to the arms of the pre-formed three-way junction core via two-way junctions to form a nanostructure.

This synthesis process is able to improve the yield of the nanostructure due to reduced amount of incomplete assemblies. Other advantages include, for example, re-use of the same core for different cargo molecules, and lower cost and easier sequence design to obtain smaller sized, less complex component strands for such nanostructures.

Example 6 Delivery of Cargo Molecule Using Multi-Way Junction

This example compares the knockdown efficiency of the siRNAs delivered by a three-way junction with the knockdown efficiency of the individual siRNAs when both were delivered with Lipofectamine.

The target was the STAT3 gene. A dual luciferase assay was used to assess the knockdown efficiency of the STAT3 siRNA. Either the three-way junction carrying the siRNA or a control siRNA without the three-way junction was co-transfected together with a dual luciferase vector encoding *Renilla* Luciferase gene with the STAT3 siRNA target site inserted the 3'UTR of the *Renilla* luciferase mRNA. Lipfectamine 2 k was used to deliver target plasmid and experimental siRNA. The three-way junction was tested at various concentrations: 2 nM, 0.4 nM and 0.08 nM. In the dual luciferase system, firefly luciferase acts as an internal control for RNAi activity against *Renilla* luciferase. Readings are taken as the ratio between *Renilla* and firefly luminescence. As expected, no consistent luminescence change was observed in the firefly control, and *Renilla* to firefly ratio changed in response to siRNAs, indicating targeted knockdown. For STAT3 target plasmid only, luminescence (the *Renilla* to firefly ratio) was normalized at 100% with STAT3 target plasmid only without siRNA.

Individual STAT3 siRNAs were used as a positive control, which demonstrated high knockdown efficiency. Individual HDAC8 siRNA was used as a negative control, which showed no knockdown when used with STAT3 target plasmid and luminescence levels similar to the STAT3 target plasmid only.

Figure 21:
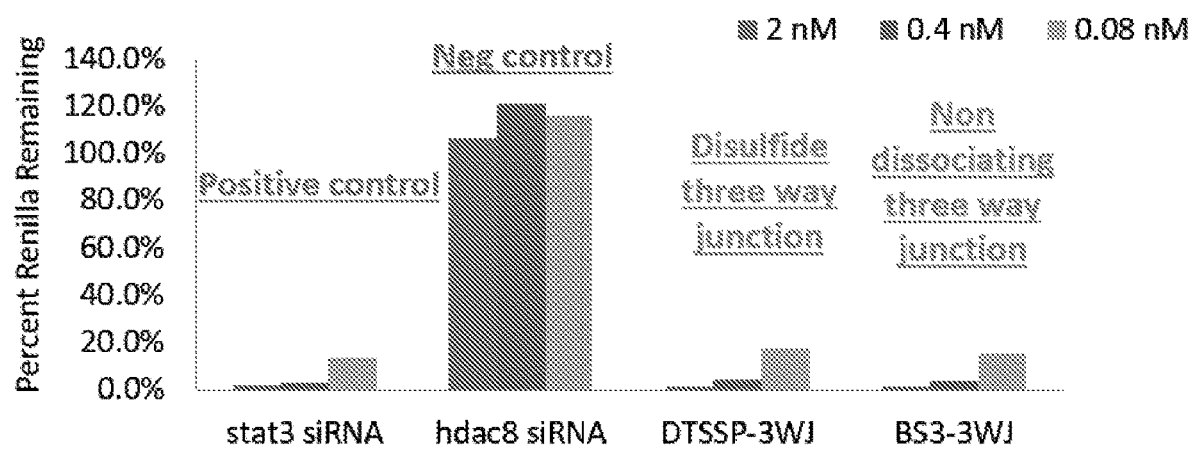
FIG. 21 shows that dissociating and non-dissociating three-way junctions demonstrated similar knockdown efficiency when transfected with L2K. The results of dual luciferase readout for STAT3 at 48 hours are shown in the figure. BS3 (Sulfo-DSS) is bis(sulfosuccinimidyl)suberate, an amine-to-amine crosslinker that is homobifunctional, water-soluble, non-cleavable and membrane impermeable.

As demonstrated in FIG. 21, the three-way junction delivering a combination of two different siRNAs against two different targets achieved RNAi knockdown against the STAT3 target that was as efficient as a STAT3 siRNA delivered by itself without any junction as a delivery vehicle. Thus, the experiment shows that the junction allowed delivery of siRNAs against combinations of targets without compromising any knockdown efficiency. Additionally, the disulfide linked three-way junction (DTSSP-3WJ) and non-dissociating three-way junction (BS3-3WJ) demonstrated similar knockdown efficiency, indicating that the mechanism of knockdown was independent from the disulfide cleavage.

Figure 22:
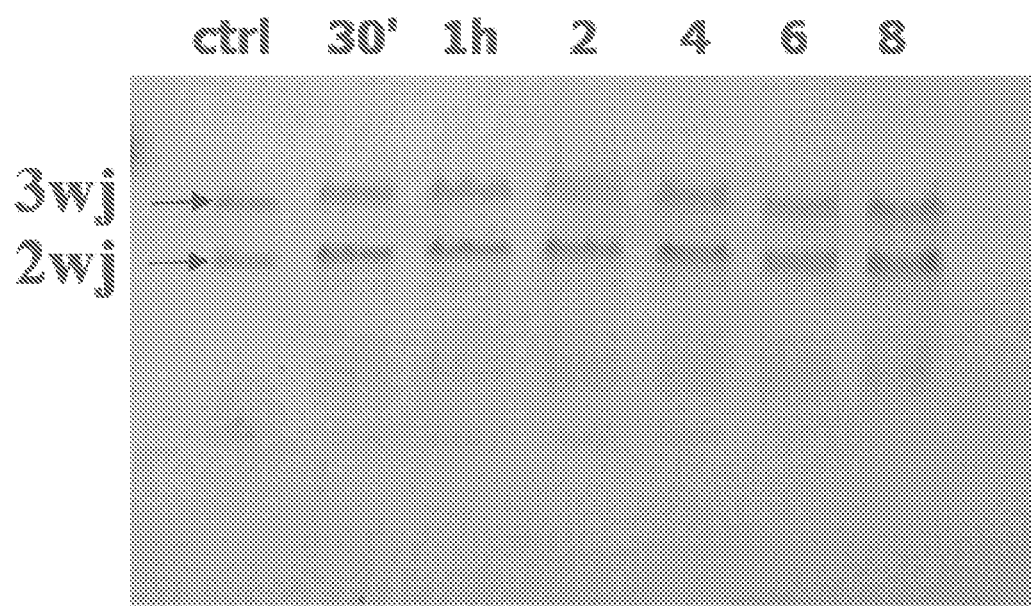
FIG. 22 shows a urea-denaturing gel electrophoresis analysis for cross-linked three-way junction and two-way junction incubated in transfection media (McCoy's media) at different time points.

As demonstrated in FIG. 22, the three-way junction and two-way junction were stable in transfection media.

REFERENCES

The references listed below, and all references cited in the specification are hereby incorporated by reference in their entireties, as if fully set forth herein.
1. Rothemund, "Folding DNA to create nanoscale shapes and patterns," *Nature* 440 (7082): 297-302 (2006).
2. Zhang et al., "Structural DNA nanotechnology: state of the art and future perspective," *J. Am. Chem. Soc.* 136 (32): 11198-211 (2014).
3. Sabir et al., "Branchpoint expansion in a fully complementary three-way DNA junction," *J. Am. Chem. Soc.* 134(14): 6280-5 (2012).
4. Bhatia et al., "A synthetic icosahedral DNA-based host-cargo complex for functional in vivo imaging," *Nature Communications* 2: 339 (2011).
5. Walsh et al., "DNA cage delivery to mammalian cells," *ACS Nano.* 5(7): 5427-32 (2011).
6. Keum et al., "Design, assembly, and activity of antisense DNA nanostructures," *Small* 7(24): 3529-35 (2011).
7. Afonin et al., "Design and self-assembly of siRNA-functionalized RNA nanoparticles for use in automated nanomedicine," *Nature Protocols* 6: 2022-2034 (2011).
8. Shu et al., "Thermodynamically stable RNA three-way junction for constructing multifunctional nanoparticles for delivery of therapeutics," *Nature Nanotechnology* 6: 658-667 (2011)
9. Lee et al., "Molecularly self-assembled nucleic acid nanoparticles for targeted in vivo siRNA delivery," *Nature Nanotechnology* 7: 389-393 (2012).
10. Fleige et al., "Stimuli-responsive polymeric nanocarriers for the controlled transport of active compounds: Concepts and applications," *Advanced Drug Delivery Reviews* 64(9): 866-884 (2012).
11. Zadeh et al., "NUPACK: analysis and design of nucleic acid systems," *J Comput Chem* 32: 170-173 (2011).
12. Dirks et al., "Thermodynamic analysis of interacting nucleic acid strands," *SIAM Rev* 49: 65-88 (2007).
13. Dirks et al., "An algorithm for computing nucleic acid base-pairing probabilities including pseudoknots," *J Comput Chem* 25: 1295-1304 (2004).

14. Dirks et al., "A partition function algorithm for nucleic acid secondary structure including pseudoknots," *J Comput Chem* 24: 1664-1677 (2003).
15. Wolf et al., "Constrained multistate sequence design for nucleic acid reaction pathway engineering," *J Am Chem Soc* 139: 3134-3144 (2017).
16. Wolf et al., "Sequence design for a test tube of interacting nucleic acid strands," *ACS Synth Biol* 4: 1086-1100 (2015).
17. Zadeh et al., "Nucleic acid sequence design via efficient ensemble defect optimization," *J Comput Chem* 32: 439-452 (2011).
18. Dirks et al., "Paradigms for computational nucleic acid design, *Nucl Acids Res* 32: 1392-1403 (2004).
19. Khvorova et al., "The chemical evolution of oligonucleotide therapies of clinical utility," *Nat Biotech* 35: 238-248 (2017).
20. Shukla et al., "Exploring Chemical Modifications for siRNA Therapeutics: A Structural and Functional Outlook," *ChemMedChem* 5, 328-349 (2010).
21. Gawande et al., "Selection of DNA aptamers with two modified bases," *Proceedings of the National Academy of Sciences* 114, 2898-2903 (2017).
22. Lu et al., "Linkers having a crucial role in antibody-drug conjugates," *International Journal of Molecular Sciences* 17: 561 (2016).
23. Aviñó et al., "Oligonucleotide-peptide conjugates: solid-phase synthesis under acidic conditions and use in ELISA assays," *Molecules* 17: 13825-13843 (2012).
24. Khvorova et al., "The chemical evolution of oligonucleotide therapies of clinical utility," *Nature Biotechnology* doi: 10.1038/nbt.3765 (2017).
25. Dowdy, "Overcoming cellular barriers for RNA therapeutics," *Nature Biotechnology* doi: 10.1038/nbt.3802 (2017).
26. Chojnowski et al., "RNA Bricks—a database of RNA 3D motifs and their interactions," *Nucleic Acids Res.* 42: D123-D121 (2014).

The invention claimed is:

1. A multi-way oligonucleotide junction for delivering one or more cargo molecules, comprising three or more oligonucleotides, wherein at least a portion of each oligonucleotide complementarily binds to a portion of another oligonucleotide to form at least three double-stranded arms, wherein at least one base pair of each of the at least three double-stranded arms is crosslinked such that the junction is stable during storage or circulation and readily dissociates upon delivery to a target, and wherein at least one of the three or more oligonucleotides comprises or is attached to at least one single-stranded overhang.

2. The junction of claim 1, wherein each of the three or more oligonucleotides is a DNA, an RNA, or a synthetic oligonucleotide.

3. The junction of claim 1, wherein one or more of the at least one single-stranded overhang comprises or is attached to at least one of the one or more cargo molecules.

4. The junction of claim 1, wherein one ore more of the at least one single-stranded overhang binds to a single-stranded nucleic acid that comprises or is attached to at least one of the one or more cargo molecules.

5. The junction of claim 1, wherein each of the at least three double-stranded arms has a length of between 3 base pairs and 15 base pairs.

6. The junction of claim 1, wherein each of the at least three double-stranded arms has a length of 7 base pairs.

7. The junction of claim 1, wherein the extremity of one or more of the at least three double-stranded arms is cross-linked.

8. The junction of claim 1, wherein the extremity of one or more of the at least three double-stranded arms is cross-linked with a cross-linker containing a disulfide bond.

9. The junction of claim 8, wherein the cross-linker is 3,3'-dithiobis(sulfosuccinimidylpropionate) (DTSSP).

10. The junction of claim 1, wherein at least one of the one or more cargo molecules are loaded onto the junction.

11. The junction of claim 1, wherein one or more of the at least one single-stranded overhang binds to a delivery ligand for targeting a specific type of cell.

12. The junction of claim 1, wherein one or more of the at least one single-stranded overhang is a guide strand for binding to a passenger strand that is complementary to the guide strand.

13. The junction of claim 1, wherein the one or more cargo molecules includes an siRNA, a DNA aptamer, an RNA aptamer, a drug or prodrug, an antibody, an isotope or a fluorophore.

14. The junction of claim 12, wherein the guide strand comprises a sequence capable of binding to at least a portion of an mRNA encoding signal transducer and activator of transcription 3 (STAT3) or histone deacetylase 8 (HDAC8).

15. The junction of claim 1, wherein the junction is chemically modified by an amine modification, a phosphorothioate bond modification, a 2'-O-methyl modification, or a C3 spacer.

16. A nanostructure comprising two or more junctions of claim 1 attached to each other; or
   comprising at least one multi-way junction core of claim 1, and at least one two-way junction, each comprising two oligonucleotides, wherein at least a portion of each oligonucleotide complementarily bind to each other form a double-stranded arm, wherein one of the at least one two-way junction is attached to each arm of one of the at least one multi-way junction core.

17. The nanostructure of claim 16, wherein each of the at least one multi-way junction core is stabilized by one or more chemical modifications.

18. The nanostructure of claim 16, wherein one or more of the at least one two-way junction is loaded with a delivery ligand or a cargo molecule to the end not attached to the multi-way junction core.

19. The nanostructure of claim 18, wherein the cargo molecule is a Dicer-processable siRNA duplex.

\* \* \* \* \*